United States Patent
Osborne, Jr.

(10) Patent No.: US 11,612,278 B2
(45) Date of Patent: Mar. 28, 2023

(54) POWER MANAGEMENT SYSTEM FOR DISPENSERS

(71) Applicant: Charles Agnew Osborne, Jr., Cumming, GA (US)

(72) Inventor: Charles Agnew Osborne, Jr., Cumming, GA (US)

(*) Notice: Subject to any disclaimer, the term of this patent is extended or adjusted under 35 U.S.C. 154(b) by 318 days.

(21) Appl. No.: 16/732,005

(22) Filed: Dec. 31, 2019

(65) Prior Publication Data
US 2020/0205621 A1 Jul. 2, 2020

Related U.S. Application Data

(60) Provisional application No. 62/932,220, filed on Nov. 7, 2019, provisional application No. 62/787,622, filed on Jan. 2, 2019.

(51) Int. Cl.
*A47K 10/36* (2006.01)
*H04W 4/029* (2018.01)
(Continued)

(52) U.S. Cl.
CPC ............ *A47K 10/36* (2013.01); *A47K 5/1217* (2013.01); *A47K 10/3625* (2013.01); *G06K 19/07758* (2013.01); *G16H 40/20* (2018.01); *H04W 4/029* (2018.02); *H04W 52/0212* (2013.01); *A47K 2010/3226* (2013.01); *A47K 2010/3668* (2013.01)

(58) Field of Classification Search
CPC ................... A47K 10/3625; A47K 2010/3668
See application file for complete search history.

(56) References Cited

U.S. PATENT DOCUMENTS

| 5,610,589 A | 3/1997 | Evans et al. |
| 5,808,553 A | 9/1998 | Cunningham |

(Continued)

FOREIGN PATENT DOCUMENTS

| KR | 10-0990823 B1 | 10/2010 |
| WO | WO2004/086287 A2 | 10/2004 |

(Continued)

OTHER PUBLICATIONS

International Search Report and the Written Opinion of the International Search Authority for PCT/US2019/069125, dated May 7, 2020.

(Continued)

*Primary Examiner* — Timothy R Waggoner
(74) *Attorney, Agent, or Firm* — Womble Bond Dickinson (US) LLP

(57) ABSTRACT

A power management system for a dispenser that includes a passive infrared radiation sensor arranged along the dispenser and configured to detect infrared radiation emitted by one or more users within a prescribed detection range, area, or zone of the dispenser. When the passive infrared radiation sensor does not capture infrared radiation within the prescribed detection range, area, or zone, the dispenser is placed in a low power state with the passive infrared sensor remaining connected to a power source and a controller, a dispensing mechanism, and/or the proximity sensor being disconnected from the power source. Other aspects also are described.

19 Claims, 10 Drawing Sheets

(51) Int. Cl.
*G06K 19/077* (2006.01)
*G16H 40/20* (2018.01)
*A47K 5/12* (2006.01)
*H04W 52/02* (2009.01)
*A47K 10/32* (2006.01)

(56) References Cited

U.S. PATENT DOCUMENTS

| | | |
|---|---|---|
| 5,864,894 A | 2/1999 | Fedele |
| 5,900,801 A | 5/1999 | Heagle et al. |
| 5,939,974 A | 8/1999 | Heagle et al. |
| 5,945,910 A | 8/1999 | Gorra |
| 6,147,607 A | 11/2000 | Lynn |
| 6,236,317 B1 | 5/2001 | Cohen et al. |
| 6,236,953 B1 | 5/2001 | Segal |
| 6,278,372 B1 | 8/2001 | Velasco et al. |
| 6,346,886 B1 | 2/2002 | DeLaHuerga |
| 6,347,414 B2 | 2/2002 | Contadini et al. |
| 6,645,435 B2 | 11/2003 | Dawson et al. |
| 6,882,278 B2 | 4/2005 | Winings et al. |
| 6,883,563 B2 | 4/2005 | Smith |
| 6,975,231 B2 | 12/2005 | Lane et al. |
| 7,213,782 B2 | 5/2007 | Osborne et al. |
| 7,242,307 B1 | 7/2007 | LeBlond et al. |
| 7,271,719 B2 | 9/2007 | Ku et al. |
| 7,271,728 B2 | 9/2007 | Taylor et al. |
| 7,293,645 B2 | 11/2007 | Harper et al. |
| 7,312,782 B2 | 12/2007 | Hiraki et al. |
| 7,315,245 B2 | 1/2008 | Lynn et al. |
| 7,370,824 B1 | 5/2008 | Osborne |
| 7,372,367 B2 | 5/2008 | Lane et al. |
| 7,375,640 B1 | 5/2008 | Plost |
| 7,408,470 B2 | 8/2008 | Wildman et al. |
| 7,423,533 B1 | 9/2008 | LeBlond et al. |
| 7,425,900 B2 | 9/2008 | Lynn et al. |
| 7,460,013 B1 | 12/2008 | Osborne |
| 7,477,148 B2 | 1/2009 | Lynn et al. |
| 7,598,854 B2 | 10/2009 | Wong |
| 7,659,824 B2 | 2/2010 | Prodanovich et al. |
| 7,726,599 B2 | 6/2010 | Lewis et al. |
| 7,755,494 B2 | 7/2010 | Melker et al. |
| 7,770,782 B2 | 8/2010 | Sahud |
| 7,779,059 B2 | 8/2010 | Bourland et al. |
| 7,782,214 B1 | 8/2010 | Lynn |
| 7,812,730 B2 | 10/2010 | Wildman et al. |
| 7,818,083 B2 | 10/2010 | Glenn et al. |
| 7,825,812 B2 | 11/2010 | Ogrin et al. |
| 7,855,651 B2 | 12/2010 | LeBlond et al. |
| 7,893,842 B2 | 2/2011 | Deutsch |
| 7,898,407 B2 | 3/2011 | Hufton et al. |
| 7,952,484 B2 | 5/2011 | Lynn |
| 7,978,083 B2 | 7/2011 | Melker et al. |
| 8,085,155 B2 | 12/2011 | Prodanovich et al. |
| 8,094,029 B2 | 1/2012 | Ortiz et al. |
| 8,146,613 B2 | 4/2012 | Barnhill et al. |
| 8,160,742 B2 | 4/2012 | Goerg et al. |
| 8,164,439 B2 | 4/2012 | Dempsey et al. |
| 8,169,327 B2 | 5/2012 | Lynn |
| 8,196,810 B2 | 6/2012 | Sahud |
| 8,212,653 B1 | 7/2012 | Goldstein et al. |
| 8,229,185 B2 | 7/2012 | Ennis et al. |
| 8,237,558 B2 | 8/2012 | Seyed Momen et al. |
| 8,249,295 B2 | 8/2012 | Johnson |
| 8,250,657 B1 | 8/2012 | Nachenberg et al. |
| 8,264,343 B2 | 9/2012 | Snodgrass |
| 8,294,584 B2 | 10/2012 | Plost |
| 8,294,585 B2 | 10/2012 | Barnhill |
| 8,299,896 B2 | 10/2012 | Mahmoodi et al. |
| 8,334,777 B2 | 12/2012 | Wilson et al. |
| 8,344,893 B1 | 1/2013 | Drammeh |
| 8,350,706 B2 | 1/2013 | Wegelin et al. |
| 8,368,544 B2 | 2/2013 | Wildman et al. |
| 8,377,229 B2 | 2/2013 | Barnhill et al. |
| 8,395,515 B2 | 3/2013 | Tokhtuev et al. |
| 8,400,309 B2 | 3/2013 | Glenn et al. |
| 8,405,503 B2 | 3/2013 | Wong |
| 8,427,323 B2 | 4/2013 | Alper et al. |
| 8,448,848 B2 | 5/2013 | Sahud |
| 8,482,406 B2 | 7/2013 | Snograss |
| 8,498,851 B2 | 7/2013 | Ehrnsperger et al. |
| 8,502,680 B2 | 8/2013 | Tokhtuev et al. |
| 8,502,681 B2 | 8/2013 | Bolling et al. |
| 8,525,666 B2 | 9/2013 | Melker et al. |
| 8,547,220 B1 | 10/2013 | Dempsey et al. |
| 8,558,660 B2 | 10/2013 | Nix et al. |
| 8,558,701 B2 | 10/2013 | Wegelin et al. |
| 8,564,431 B2 | 10/2013 | Snodgrass |
| 8,566,478 B2 | 10/2013 | Ota et al. |
| 8,566,932 B1 | 10/2013 | Hotta et al. |
| 8,587,437 B2 | 11/2013 | Kyle et al. |
| 8,598,996 B2 | 12/2013 | Wildman et al. |
| 8,633,816 B2 | 1/2014 | Snodgrass et al. |
| 8,640,275 B2 | 2/2014 | Lawson et al. |
| 8,673,210 B2 | 3/2014 | Deshays |
| 8,674,840 B2 | 3/2014 | Snodgrass |
| 8,698,637 B2 | 4/2014 | Raichman |
| 8,717,177 B2 | 5/2014 | Cartner |
| 8,742,932 B2 | 6/2014 | Casares |
| 8,744,623 B2 | 6/2014 | Drake et al. |
| 8,746,558 B2 | 6/2014 | Healy et al. |
| 8,800,415 B2 | 8/2014 | Osborne |
| 8,922,378 B2 | 12/2014 | Raccio |
| 9,117,361 B1 | 8/2015 | Hennigan et al. |
| 9,741,233 B2 | 8/2017 | Laufer et al. |
| 9,756,992 B2 | 9/2017 | Osborne |
| 9,907,441 B2 | 3/2018 | Osborne et al. |
| 9,972,193 B2 | 5/2018 | Laufer et al. |
| 10,105,020 B2 | 10/2018 | Carper et al. |
| 10,123,665 B2 | 11/2018 | Osborne, Jr. |
| 10,136,769 B2 | 11/2018 | Osborne, Jr. et al. |
| 10,213,068 B2 | 2/2019 | Diamond |
| 10,441,117 B2 | 10/2019 | Osborne, Jr. |
| 10,446,013 B2 | 10/2019 | Laufer et al. |
| 2002/0135486 A1 | 9/2002 | Brohagen et al. |
| 2003/0019536 A1 | 1/2003 | Smith |
| 2005/0167541 A1 | 8/2005 | Osborne |
| 2005/0231373 A1 | 10/2005 | Lynn et al. |
| 2006/0173576 A1* | 8/2006 | Goerg ............... A47K 10/3662 700/236 |
| 2007/0020212 A1 | 1/2007 | Bernal et al. |
| 2007/0096930 A1 | 5/2007 | Cardoso |
| 2007/0229288 A1 | 10/2007 | Ogrin et al. |
| 2007/0247316 A1 | 10/2007 | Wildman et al. |
| 2008/0001763 A1 | 1/2008 | Raja et al. |
| 2008/0087719 A1 | 4/2008 | Sahud |
| 2008/0100441 A1 | 5/2008 | Prodanovich et al. |
| 2008/0126126 A1 | 5/2008 | Ballai |
| 2008/0136649 A1 | 6/2008 | Van De Hey |
| 2008/0303658 A1 | 12/2008 | Melker et al. |
| 2009/0091458 A1 | 4/2009 | Deutsch |
| 2009/0189759 A1 | 7/2009 | Wildman et al. |
| 2009/0195385 A1 | 8/2009 | Huang et al. |
| 2009/0224907 A1 | 9/2009 | Sinha et al. |
| 2009/0224924 A1 | 9/2009 | Thorp |
| 2009/0267776 A1 | 10/2009 | Glenn |
| 2009/0272405 A1 | 11/2009 | Barnhill et al. |
| 2009/0273477 A1 | 11/2009 | Barnhill |
| 2010/0073162 A1 | 3/2010 | Johnson et al. |
| 2010/0090837 A1 | 4/2010 | Jung et al. |
| 2010/0094581 A1 | 4/2010 | Cagle |
| 2010/0117823 A1 | 5/2010 | Wholtjen |
| 2010/0155416 A1 | 6/2010 | Johnson |
| 2010/0164728 A1 | 7/2010 | Plost |
| 2010/0231385 A1 | 9/2010 | Melker et al. |
| 2010/0238021 A1 | 9/2010 | Harris |
| 2010/0265059 A1 | 10/2010 | Melker et al. |
| 2010/0328076 A1 | 12/2010 | Kyle et al. |
| 2011/0018998 A1 | 1/2011 | Guzik |
| 2011/0057799 A1 | 3/2011 | Taneff |
| 2011/0121974 A1 | 5/2011 | Tenarvitz et al. |
| 2011/0125524 A1 | 5/2011 | Tenarvitz et al. |
| 2011/0169643 A1 | 7/2011 | Cartner |
| 2011/0169645 A1 | 7/2011 | Cartner et al. |
| 2011/0169646 A1 | 7/2011 | Raichman |

(56) References Cited

U.S. PATENT DOCUMENTS

| | | |
|---|---|---|
| 2011/0193703 A1 | 8/2011 | Payton et al. |
| 2011/0205061 A1 | 8/2011 | Wilson et al. |
| 2011/0254682 A1 | 10/2011 | Sigrist Christensen |
| 2011/0271441 A1 | 11/2011 | Bayley et al. |
| 2011/0273298 A1 | 11/2011 | Snodgrass et al. |
| 2011/0291841 A1 | 12/2011 | Hallock et al. |
| 2011/0297830 A1* | 12/2011 | Willden .............. G08B 13/191 250/338.1 |
| 2011/0316695 A1 | 12/2011 | Li et al. |
| 2011/0316701 A1 | 12/2011 | Alper et al. |
| 2011/0316703 A1 | 12/2011 | Butler et al. |
| 2012/0013470 A1 | 1/2012 | Lynn |
| 2012/0055986 A1 | 3/2012 | Sahud |
| 2012/0062382 A1 | 3/2012 | Taneff |
| 2012/0112906 A1 | 5/2012 | Borke et al. |
| 2012/0112914 A1 | 5/2012 | Wegelin et al. |
| 2012/0158419 A1 | 6/2012 | Nuthi |
| 2012/0253510 A1 | 10/2012 | Thomas et al. |
| 2012/0256742 A1 | 10/2012 | Snodgrass et al. |
| 2012/0268277 A1 | 10/2012 | Best |
| 2012/0270261 A1 | 10/2012 | Mayer et al. |
| 2012/0274468 A1 | 11/2012 | Wegelin et al. |
| 2012/0303159 A1 | 11/2012 | Drake et al. |
| 2012/0312853 A1 | 12/2012 | Osborne et al. |
| 2013/0025714 A1 | 1/2013 | Hermann |
| 2013/0027199 A1 | 1/2013 | Bonner |
| 2013/0033376 A1 | 2/2013 | Seyed Momen et al. |
| 2013/0035900 A1 | 2/2013 | Purcell et al. |
| 2013/0038446 A1 | 2/2013 | Huseth et al. |
| 2013/0045685 A1 | 2/2013 | Kiani |
| 2013/0067658 A1 | 3/2013 | Loberger et al. |
| 2013/0076514 A1 | 3/2013 | Wegelin et al. |
| 2013/0113619 A1 | 5/2013 | Snodgrass |
| 2013/0120120 A1 | 5/2013 | Long et al. |
| 2013/0187779 A1 | 7/2013 | Pokraiae |
| 2013/0218583 A1 | 8/2013 | Marcolongo et al. |
| 2013/0229276 A1 | 9/2013 | Hunter |
| 2013/0234855 A1 | 9/2013 | Knighton |
| 2013/0257615 A1 | 10/2013 | Iseri et al. |
| 2013/0262034 A1 | 10/2013 | Iseri et al. |
| 2013/0268293 A1 | 10/2013 | Knudson et al. |
| 2013/0291947 A1 | 11/2013 | Chandler et al. |
| 2013/0320130 A1 | 12/2013 | Osborne |
| 2014/0009292 A1 | 1/2014 | Long et al. |
| 2014/0015670 A1 | 1/2014 | Wegelin et al. |
| 2014/0022073 A1 | 1/2014 | Balinski et al. |
| 2014/0022074 A1 | 1/2014 | Balinski et al. |
| 2014/0035744 A1 | 2/2014 | Wildman et al. |
| 2014/0046722 A1 | 2/2014 | Rosenbloom et al. |
| 2014/0049391 A1 | 2/2014 | Bolling et al. |
| 2014/0069951 A1* | 3/2014 | Schmidt ................ A47K 10/32 221/13 |
| 2014/0104062 A1 | 4/2014 | Weiner |
| 2014/0139339 A1 | 5/2014 | Jones et al. |
| 2014/0167917 A2 | 6/2014 | Wallace et al. |
| 2014/0240131 A1* | 8/2014 | Raccio ................ G08B 21/245 340/573.1 |
| 2014/0263812 A1 | 9/2014 | Osborne |
| 2014/0300735 A1 | 10/2014 | Reibel et al. |
| 2015/0022025 A1* | 1/2015 | Lee ........................ G06Q 50/06 307/116 |
| 2015/0297043 A1 | 10/2015 | Osborne et al. |
| 2016/0005300 A1 | 1/2016 | Laufer et al. |
| 2016/0325957 A1 | 11/2016 | Borke |
| 2016/0353945 A1 | 12/2016 | Osborne |
| 2016/0353946 A1 | 12/2016 | Osborne |
| 2016/0353947 A1 | 12/2016 | Osborne |
| 2017/0051486 A1* | 2/2017 | Schomburg .............. E03D 7/00 |
| 2017/0112335 A1 | 4/2017 | Diamond |
| 2017/0365159 A1 | 12/2017 | Laufer et al. |
| 2017/0367547 A1 | 12/2017 | Osborne |
| 2018/0153360 A1 | 6/2018 | Osborne, Jr. et al. |
| 2018/0170703 A1 | 6/2018 | Osborne, Jr. |
| 2018/0263433 A1 | 9/2018 | Osborne, Jr. |
| 2018/0293873 A1* | 10/2018 | Liu .................... G06K 7/10366 |
| 2018/0315293 A1 | 11/2018 | Laufer et al. |
| 2019/0350414 A1* | 11/2019 | Starkey .............. A47K 10/3687 |
| 2020/0205620 A1 | 7/2020 | Osborne, Jr. |
| 2021/0330142 A1 | 10/2021 | Osborne, Jr. |

FOREIGN PATENT DOCUMENTS

| | | |
|---|---|---|
| WO | WO2010/099488 A1 | 9/2010 |
| WO | WO2013/058957 A2 | 4/2013 |
| WO | WO2018/216015 A1 | 11/2018 |

OTHER PUBLICATIONS

Adafruit PIR Motion Sensor; "How PIRs Work"; https://learn.adafruit.com/pir-passive-infared-proximity-motion-sensor?view=all#how-pirs-work; Jan. 28, 2014.

El-Pro-Cus; Electronics Projects Focus; "PIR Sensor—Basic & Applications"; https://www.elprocus.com/pir-sensor-basics-applications/; Oct. 2013.

Wikipedia; "Passive infared sensor"; available as of Oct. 31, 2007 (last edited Feb. 2020).

Internet Archive; Wayback Machine; Wikipedia; Passive infrared sensor; https://en.wikipedia.org/wiki/Passive_infrared_sensor; https://web.archive.org/web/20071031191047/https://en.wikipedia.org/wiki/Passive_infrared_sensor; Oct. 31, 2013.

Extended European Search Report regarding related Application No. EP19907795.9 dated Sep. 27, 2022.

Partial Supplementary European Search Report regarding related Application No. EP19907898.1 dated Jul. 26, 2022.

* cited by examiner

POWER MANAGEMENT SYSTEM FOR DISPENSERS

CROSS REFERENCE TO RELATED APPLICATIONS

The present Patent Application claims the benefit of U.S. Provisional Patent Application No. 62/932,220, filed Nov. 7, 2019, and of U.S. Provisional Patent Application No. 62/787,622, filed Jan. 2, 2019.

INCORPORATION BY REFERENCE

U.S. Provisional Patent Application No. 62/932,220, filed Nov. 7, 2019, and U.S. Provisional Patent Application No. 62/787,622, filed Jan. 2, 2019, are specifically incorporated by reference herein as if set forth in their entireties.

TECHNICAL FIELD

This disclosure generally relates to dispensers and, more particularly, to electronic dispensers for flexible sheet materials, such as paper products, or electronic dispensers for liquids, such as liquid soaps or hand sanitizers. Other aspects are also described.

BACKGROUND

Automated sheet material (e.g., paper towels, tissue, etc.) and fluid dispensers (e.g., liquid soap, hand sanitizer, etc.) are in wide use in a variety of public or commercial environments for sanitary and hygiene purposes and to help control the amounts of paper or fluids dispensed. In addition, to control the amounts of sheet material or fluids dispensed per operation/use of these dispensers, energy consumption and conservation of battery life for such automated sheet material and fluid dispensers is important, as over-use will lead to increased loss of battery power, which can cause disruptions in operation or mis-feeding issues. A major drawback to some automated dispensers is the steady state current battery life consumption percentage, due to the dispenser being in a substantially active state and always looking for the next user. Such steady state current consumptions often can utilize upwards of 50 to 80% of a dispenser's battery capacity, depending on actual daily use. Such power drains/consumption can be more problematic in smaller dispenser units, for example, in dispensers used in residential and/or low traffic areas where smaller size batteries, i.e., "C" or "D" cell batteries, generally are used due to size, by requiring closer monitoring and more frequent change-out of spent batteries.

Accordingly, it can be seen that a need exists for systems and methods for dispensers that helps to drastically reduce steady state current consumption, while allowing the dispenser to respond to any user at any time. The present disclosure addresses these and other related and other related issues in the art.

SUMMARY

Briefly described, the present disclosure is directed to dispensers such as for dispensing selected amounts of a sheet material, for example, paper products, including paper towels, tissue, napkins, etc., or dispensing liquids, e.g., liquid soap, hand sanitizers, etc. The dispenser can include a dispenser housing with a supply of a fluid or a sheet material to be dispensed in metered, predetermined amounts.

In one construction, the dispenser can include a sheet material dispenser with a roll of sheet material attached to at least a portion of the dispenser housing, for example, using one or more arms or supports. The sheet material dispenser further may include a feed roller that is rotatably mounted within the dispenser housing and generally feeds or drives a predetermined amount of sheet material of the supply of sheet material through a discharge chute of the dispenser. The sheet material dispenser also generally can include one or more pressing rollers that can engage, urge, bias and/or press the sheet material against the feed roller such that the sheet material is pulled or drawn therebetween during a dispensing operation. The sheet material dispenser can include an automatic drive assembly/system for driving rotation of the feed roller to dispense selected amounts of sheet material. The drive system/assembly can include at least one driving mechanism, including a motor in communication with the feed roller to drive rotation or movement thereof.

In another construction, the dispenser can include a liquid dispenser with a dispenser housing that supports a supply chamber or reservoir containing a liquid, e.g., liquid soap, hand sanitizer, etc. for dispensing thereof. The liquid dispenser further includes one or more nozzles or other discharge outlets for dispensing the liquid to users (e.g., upon activation of one or more sensors or other activation mechanisms). The fluid dispenser also includes a pumping mechanism, e.g., including pumps or other suitable actuators, for directing the fluid from the supply chamber to the discharge outlet(s).

According to embodiments of the present disclosure, the dispenser (e.g., the sheet material, fluid dispenser, or other type of dispenser) also includes a power management system configured to control activation and/or deactivation of the dispenser based on a detected presence of a user within a prescribed area or zone around the dispenser. For example, the power management system can include one or more sensors, e.g., passive infrared radiation ("PIR") sensors, that use infrared radiation to detect people/users as they enter and exit a prescribed or focused area or zone where the dispenser is located, e.g., a restroom, hospital room, etc. The power management system further is in communication with the dispenser circuitry/controller to selectively activate the circuitry based on the detected presence of people/users by the infrared radiation sensor(s).

In operation, if a user is not detected, the power management system can initially place the dispenser/controller into a low power mode, in which the controller is deactivated or placed into an inactive state, e.g., a switch or connection may be opened so as to disconnect or decouple the controller from the dispenser's power source, such that the primary components of the dispenser, with the exception of one or more passive infrared sensors, are not drawing power when not in operation.

That is, when a user/person enters the area or zone covered by the one or more infrared radiation sensors, the power management system activates the dispenser controller to allow normal function of the dispenser, such as by closing or otherwise engaging the switch to couple or connect the controller to the power source). And, when the user is no longer within the area or zone covered by the one or more infrared sensors, i.e., no infrared detection is made by the sensor(s) for a prescribed period of time, the power management system can return dispenser back to the low power mode once the user has left the area/zone of use. As a result, the amount of power used by the dispenser on a per period (i.e., hourly, daily, etc.) basis can be substantially reduced, and during periods when no user is nearby (e.g., at night, when the location of the dispenser is unoccupied, etc.), the power consumption can be reduced to a minimum level needed to power just the one or more passive infrared sensors with the other operative components (controller, driving mechanism, proximity sensors, monitor system, etc.) shut down and substantially out of communication with the power source.

In one aspect, the present disclosure is directed to a dispenser with a power management system. The dispenser comprises a supply of liquid or sheet material, and a dispenser housing in which the supply is received. The dispenser includes a dispensing mechanism located within the dispenser housing in communication with the supply and configured to dispense prescribed amounts of the supply from the dispenser housing. The dispenser also has a proximity sensor positioned along the dispenser housing and configured to detect a presence of a user proximate the dispenser. The dispenser further includes a controller in communication with the dispensing mechanism and the proximity sensor. The controller is configured to activate the dispensing mechanism to dispense the prescribed amounts of the supply upon receipt of one or more signals from the proximity sensor indicative of the presence of the user proximate the dispenser. In addition, the dispenser includes a power source supplying power to the controller, dispensing mechanism and proximity sensor.

The dispenser also comprises a power management system in communication with the controller and having a passive infrared radiation sensor arranged along the dispenser housing and configured to detect infrared radiation emitted by one or more users within a prescribed detection range, area, or zone of the dispenser. When the passive infrared radiation sensor does not capture infrared radiation within the prescribed detection range, area, or zone, the dispenser is placed in a low power state with the passive infrared sensor remaining connected to the power source and the controller, the dispensing mechanism, and/or the proximity sensor being disconnected from the power source. But, when the at least one passive infrared radiation sensor captures infrared radiation within the prescribed detection range, area, or zone, the controller, the dispensing mechanism, and/or the proximity sensor are connected with the power source.

The dispenser further can comprise a switch coupled to the power source and the controller, proximity sensor, and/or the dispensing mechanism. The switch is responsive to one or more signals from the passive infrared radiation sensor to decouple the power source from the controller, proximity sensor, and/or the dispensing mechanism, such that the controller, proximity sensor, and/or the dispensing mechanism do not consume power from the power source. In one embodiment, the switch can comprise a triode.

In some embodiments, when the passive infrared radiation sensor does not capture infrared radiation within the prescribed detection range, area, or zone, the passive infrared radiation sensor outputs one or more low level signals to the controller. Upon receipt of the one or more low level signals from the passive infrared radiation sensor at the controller, the controller initiates a shutdown sequence to complete any ongoing work, functions, or operations of the controller. Upon completion of the shutdown sequence, the controller outputs one or more low level signals to the switch such that the switch decouples the power source and the controller, proximity sensor, and/or the dispensing mechanism.

In one embodiment, the dispenser consumes less than about 100 µA in the low power state. In another embodiment, the dispenser consumes less than about 50 µA in the low power state. In yet another embodiment, the dispenser consumes less than about 30 µA to less than about 20 µA in the low power state.

The dispenser further can include a passive infrared radiation sensor controller that is integrated with the passive infrared radiation sensor. The passive radiation sensor controller is configured to generate one or more signals responsive to signals received from the passive infrared radiation sensor to connect and disconnect the controller, dispensing mechanism, and proximity sensor to and from the power source.

The dispenser further can include a timer that is integrated with the passive infrared radiation sensor. The timer can be activated when the passive infrared radiation sensor does not detect infrared radiation within the prescribed detection range, area, or zone. Upon expiration of the timer, the power source can be disconnected from the controller, proximity sensor, and/or the dispensing mechanism.

In one embodiment, the dispenser includes a sheet material dispenser, and the dispensing mechanism includes a feed roller that is configured engage and move sheet material from the supply of sheet along a discharge path and out of the dispenser for dispensing thereof.

In another embodiment, the dispenser includes a liquid dispenser. In this embodiment, the supply of liquid includes a supply chamber that stores a liquid, while the dispensing mechanism includes a pump that directs or moves the liquid from the supply chamber to the discharge.

In another aspect, the present disclosure is directed to a dispensing system comprising a lead dispenser and a plurality of drone dispensers. The lead dispenser can include a controller for controlling one or more operations of the lead dispenser, and at least one passive infrared radiation sensor in communication with the controller. The passive infrared radiation sensor is configured to capture infrared radiation indicative of one or more individuals present within a prescribed detection range, area, or zone of the lead dispenser.

The plurality of drone dispensers each are configured to communicate information to the lead dispenser. Each of the plurality of drone dispensers include a controller for controlling one or more operations of each done dispenser and a passive infrared radiation sensor in communication with the controller of each drone dispenser. The passive infrared radiation sensor of each drone dispenser is configured to capture infrared radiation indicative of one or more individuals present within a prescribed detection range, area, or zone of each drone dispenser. When the passive infrared radiation sensor of one of the drone dispensers does not capture infrared radiation, the controller of that drone dispenser is disconnected from a power source thereof.

The dispensing system also comprises a network in communication with the lead dispenser. The lead dispenser is configured to communicate information related to the lead dispenser and the information received from the plurality of drone dispensers to the network.

With the dispensing system, a power source of the lead dispenser remains connected to the controller of the lead dispenser when passive infrared radiation sensors of the lead dispenser or of any of the plurality of drone dispensers capture infrared radiation indicative of one or more individuals present within the prescribed range, area or zone thereof.

In embodiments, one or more of the plurality of drone dispensers includes a sheet material dispenser, and/or one or more of the plurality of drone dispensers includes a liquid dispenser.

In addition, the plurality of drone dispensers can transmit one or more alerts or notifications to the lead dispenser if the one or more drone dispensers are experiencing an error condition, a low power condition, and/or a low supply condition, and the lead dispenser can transmit the one or more alerts or notifications from the plurality of drone dispensers to the network.

The lead dispenser also can include a long range transmitter/receiver that facilitates communication between the lead dispenser and the network.

These and other advantages and aspects of the embodiments of the disclosure will become apparent and more readily appreciated from the following detailed description of the embodiments and the claims, taken in conjunction with the accompanying drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the embodiments of the present disclosure, are incorporated in and constitute a part of this specification, illustrate embodiments of the invention, and together with the detailed description, serve to explain the principles of the embodiments discussed herein. No attempt is made to show structural details of this disclosure in more detail than may be necessary for a fundamental understanding of the exemplary embodiments discussed herein and the various ways in which they may be practiced.

DETAILED DESCRIPTION

The following description is provided as an enabling teaching of embodiments of this disclosure. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances. Thus, the following description is provided as illustrative of the principles of the embodiments of the present disclosure and not in limitation thereof.

Figure 1A:
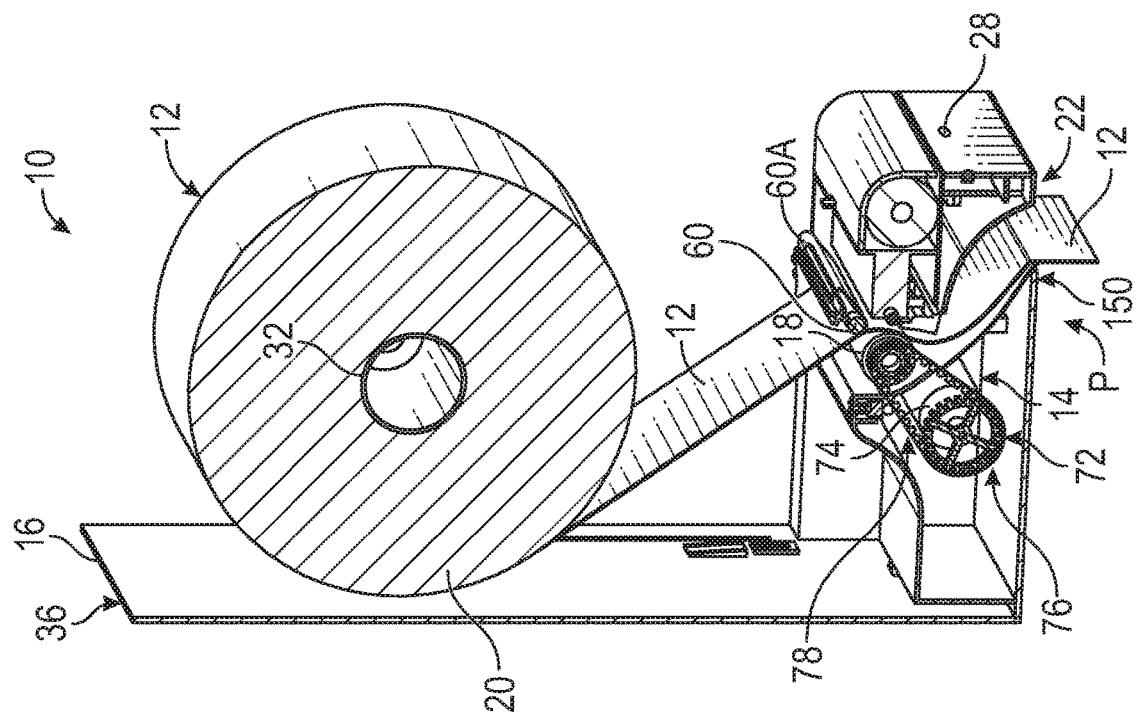
FIGS. 1A-C shows a perspective, partial cutaway views of an example sheet material dispenser according to principles of the present disclosure.
Figure 1B:
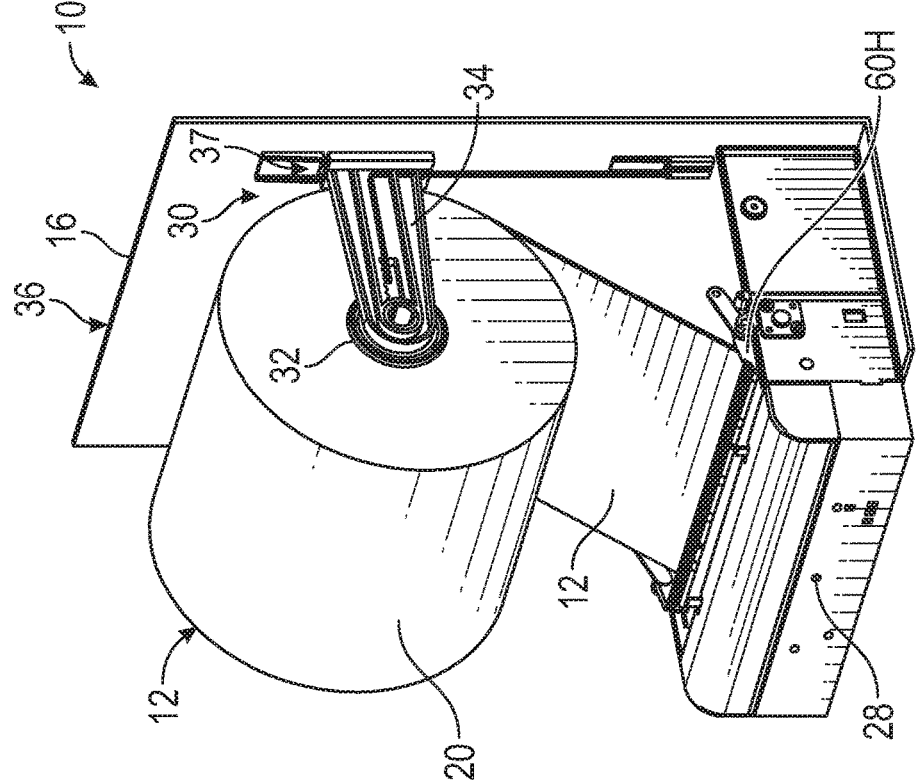
Figure 1C:
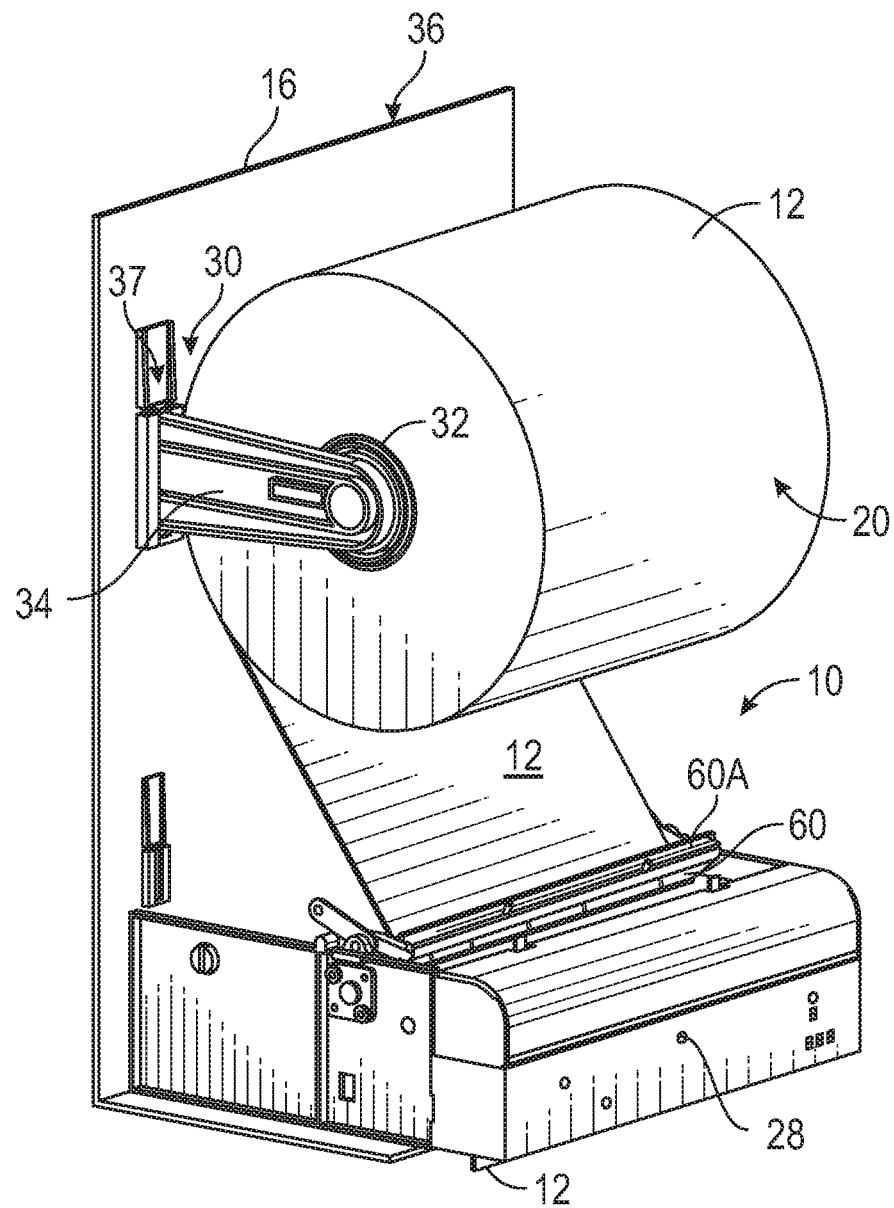

As generally illustrated in FIGS. 1A-1C and 3, the present disclosure is directed to dispensers that can be automated dispensers 10 for feeding or dispensing a flexible sheet material 12, or dispensers 300 for dispensing fluid materials. In one aspect, as shown in FIGS. 1A-1C, the dispenser 10 can dispense various types of sheet materials including paper sheet materials, such as towels, tissue, napkins, etc. The dispenser 10 generally will include a dispensing mechanism including driven feed roll drive assembly/system 14 mounted or otherwise disposed within a dispenser housing 16 and operable to dispense prescribed amounts/lengths of sheet material. For example, upon activating the dispenser 10, the feed roller drive assembly 14 is engaged and operates to drive or cause rotation of a feed roller or drive spindle 18. The rotation of the feed roller 18 in turn pulls the sheet material 12 from a supply of sheet material 20 for feeding a predetermined, prescribed, measured or selected amount or length L (e.g., a 10"-12" or other desired length) of sheet material 12 along a conveying or feed path P (FIG. 1B) from the roll or supply 20 of the sheet material 12 through and out of a discharge, such as a discharge chute 22 or other suitable opening provided/defined in the housing 16 of the dispenser 10, as is generally indicated in FIG. 1B.

Figure 4:
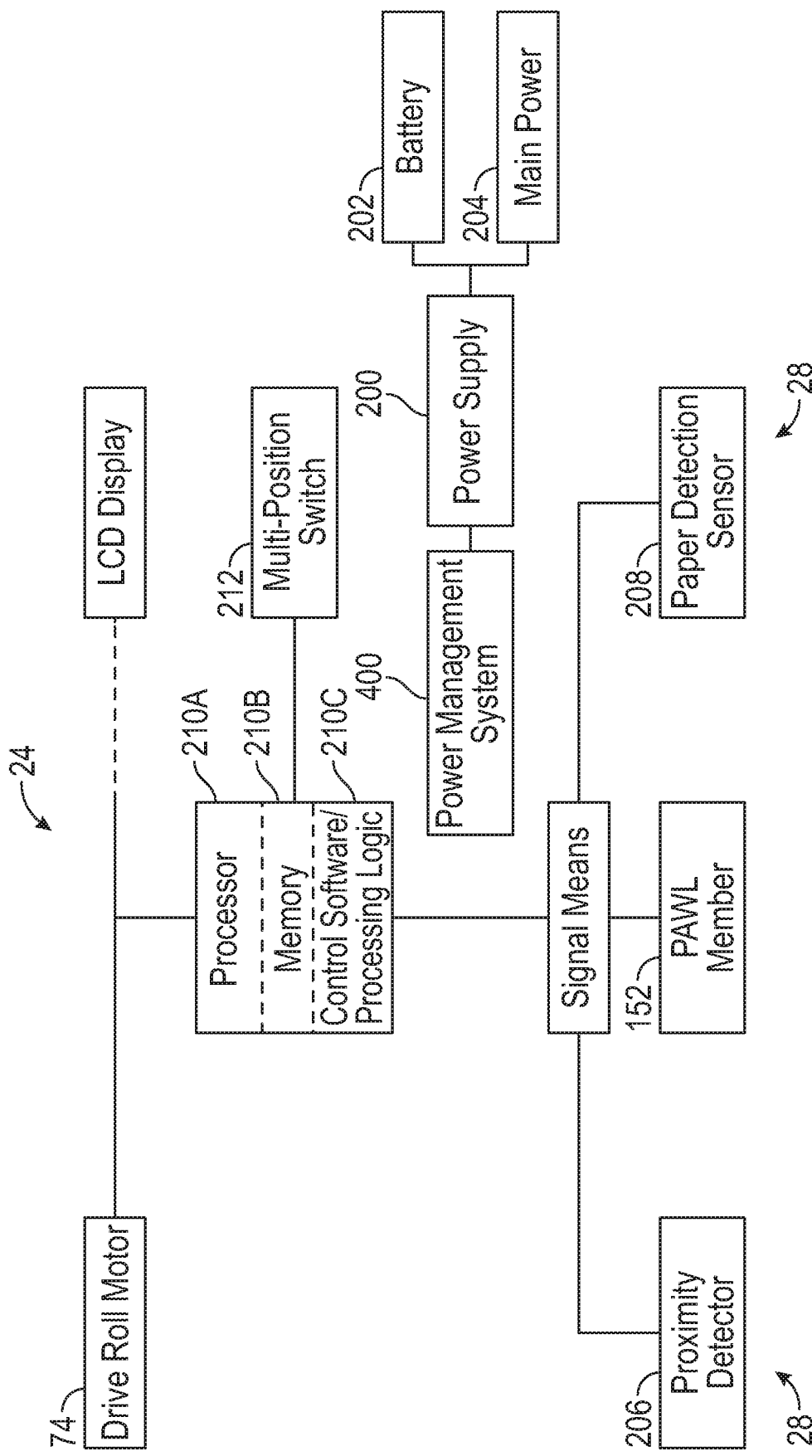
FIG. 4 shows a block diagram of an example of a control system in communication with the dispenser according to one aspect of the present disclosure.

The feed roller drive assembly 14 can be activated and driven/rotated to pull and feed the sheet material 12 from the sheet material supply 20 to and through the discharge chute 22 upon receiving a signal from a control system or control circuit 24 of the dispenser 10. An example of a control system 24 for a dispenser is generally shown in FIG. 4. The control system 24 can include a controller or control unit 210 including a processor 210A, such as a microprocessor, CPU, etc., a memory 210B, and computer programming 210C stored in the memory 210B and executed by the processor 210A for control of the feed roller drive assembly 14 to feed the selected or desired length of sheet material and to monitor the dispenser 10 and components such as the supply of sheet material and usage/operation of the dispenser. The controller 210 further will be in communication with, and will receive a plurality of signals, from a sensor or an array or series of sensors, such as generally indicated at 28, to control dispensing of the sheet material 12.

The sensors 28 can include various type sensors or detectors, for example, including an adjustable proximity sensor that can be configured/adjusted to detect the presence of a user's hand or other object at a desired range/location and dispense measured/selected amounts of sheet material 12. The proximity sensor can be manually or automatically adjustable. In addition, or in the alternative, one or more pairs of IR sensors (e.g., an emitter and a corresponding detector) that are arranged about/within the discharge chute 22 and transmit/receive signals across the discharge path P to sense or detect the presence or absence of sheet material or other object within the discharge chute or otherwise along the feed path. Any suitable sensor, however, such as a photoelectric, light curtain, or other similar sensing systems/detectors, can be used to detect the presence of a user's hands or other object placed along the dispenser housing 16, and/or the feeding of a selected amount of sheet material 12 can be used, without departing from the present disclosure. In addition, various sensor arrays and/or control systems can be used, such as disclosed in U.S. patent application Ser. No. 15/185,937, and U.S. patent application Ser. No. 14/256, 019, the complete disclosures of which are incorporated by reference as if set forth fully herein.

It further should be appreciated that the sheet material dispenser 10 described herein should not be considered to be limited to any particular style, configuration, or intended use, or to a particular type of sheet material. For example, the dispenser 10 may be operable to dispense paper towels, toilet tissue, or other similar paper or sheet materials, including dispensing or feeding non-perforated and/or perforated sheet materials.

As indicated in FIGS. 1A and 1C, the dispenser housing 16 includes a roll support mechanism 30, for holding at least one roll 32 of the supply 20 of sheet material 12. The roll support mechanism 30 can include a pair of supports or arms 34 coupled to the dispenser housing 16 and supporting the roll 32, such as indicated at 36. These arms/supports 34 may be fixedly arranged to hold the supply 20 of sheet material in a spaced relationship with respect to the feed roller 18. For example, the support arms 34 can be attached or coupled to the dispenser housing 16 by sliding or snap-fitting at least a portion of the supports/arms within grooves or slots 37 defined along a rear portion 36 of the dispenser housing 16. However, the support arms 34 can be connected to the dispenser housing 16 in any suitable manner, such as with one or more fasteners or other suitable connection mechanisms. As a further alternative, the support arms also can be integrally formed with the housing without departing from the present disclosure. In additional or alternative constructions, the support arms 34 also may be biased or urged, such as by a spring or other suitable biasing mechanism(s), or by a general resiliency, toward the feed roller 18 to urge or direct the supply 20 of sheet material downwardly toward or against the feed roller 18.

The feed roller 18 is movably or rotatably coupled to one or more walls or other portions of the dispenser housing 16. For example, the ends of the feed roller 18 can be connected, mounted, or otherwise coupled to the dispenser housing 16 by one or more bearing assemblies and/or other suitable support mechanisms that support and allow for rotation of the feed roller 18 in relation to the dispenser housing 16.

As illustrated in FIG. 1B, the dispenser assembly 10 further generally can include one or more pressing rollers 60. The pressing rollers 60 can be biased toward engagement with the feed roller 18, so as to engage and urge or press the sheet material 12 against the feed roller 18 with a force sufficient to draw or pull the sheet material 12 therebetween upon rotation of the feed roller 18. The pressing roller(s) 60 can be mounted within the dispenser housing 16, such as with the ends thereof held within one or more arms or supports of a bracket 60A in a manner to enable rotation of the pressing roller(s) 60. The bracket 60A also can be biased by a biasing member, such as a spring, so that the pressing rollers 60 can be urged toward the driven feed roller 18. Additionally, or in the alternative, one or more pressing roller(s) 60 further can be disposed within a frame or other structure and biased toward the feed roller 18 such as by compressing/tension springs or other suitable springs, biased cylinders or other biasing mechanisms. In one construction, the frame can support at least two pressing rollers and also can be pivotable to enable one pressing roller to move away from the feed roller as needed, while the other roller is pivoted into closer contact with the feed roller (not shown). In addition, or alternatively, the pressing rollers 60 may be driven by drive mechanism, for example, off of the motor that drives the feed roller or by a separate drive, so as to facilitate feeding of the sheet material 12.

The feed roller drive assembly 14 includes at least one driving mechanism, e.g., a motor 74, that is in communication with the feed roller 18 so as to drive movement/rotation thereof (FIG. 1C). The motor 74 can include a brushless servo or stepper motor or other, similar type of variable speed electric motor, and communicates with the control system 24 of the dispenser 10 to receive instructions and power for activating and driving the feed roller 18 through a dispensing cycle (e.g., a determined time, number of revolutions, etc.), so as to feed the selected or desired amount/length of the sheet material through the discharge chute 22 of the dispenser 10. In one additional aspect, the drive system/assembly 14 also can include a transmission assembly 76 for transferring power between the motor 74 and the feed roller 18. For example, the transmission assembly 76 can include a drive belt 78 and/or drive gears coupling the motor 74 to the feed roller 18. In alternative constructions, the feed roller drive assembly 14 can include a gear assembly including a plurality of intermeshing gears that operatively connect the driving mechanism 74 and the feed roller 18. Any suitable transmission mechanisms, device, assemblies, etc. can be used for transferring power between the driving mechanism and the feed roller, without departing from the scope of the present disclosure.

The sheet material dispenser 10 also can include a cutting mechanism/assembly 150 for cutting or severance of dispensed sheet material. In one embodiment, as shown in FIGS. 2A and 2B, the dispenser housing may include one or more tear bars or other suitable cutting members 151 disposed adjacent or along the dispenser housing 16 so that a user can separate a sheet or measured amount of the material by grasping and pulling the sheet across the tear bar 151.

Figure 2A:
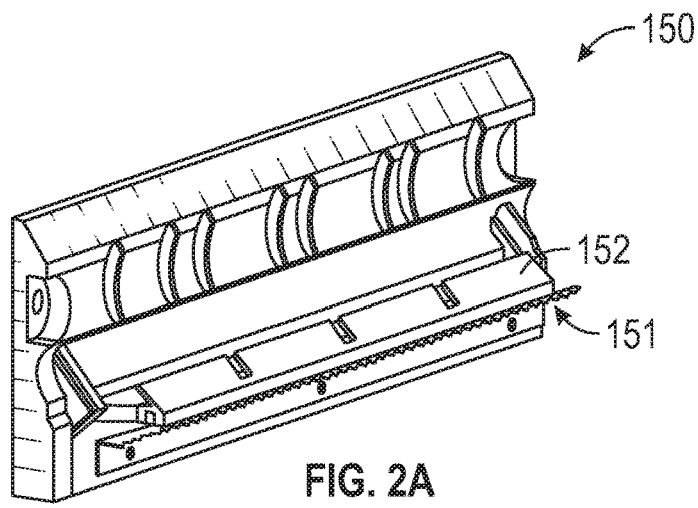
FIGS. 2A-2B provide examples of a tear bar and pivotable pawl member that can be provided for assisting in control of the dispenser according to aspects of the present disclosure.
Figure 2B:
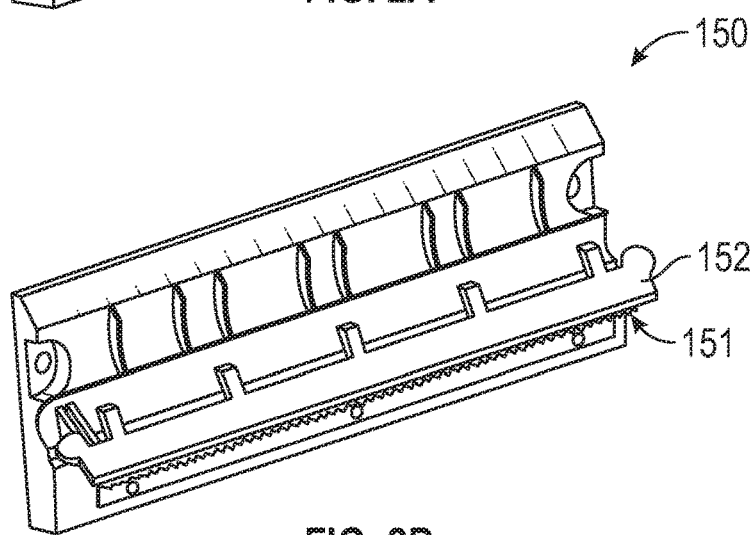

In addition, as also shown in FIGS. 2A and 2B, a pivotally mounted pawl member 152 can be located proximate to the stationary tear bar 151 such that movement of sheet material 12 into the tear bar 151 for severance pivots the pawl member 152 between multiple positions. A signal device such as a proximity sensor switch or the like, cooperative with the pawl member 152, can also be arranged such that movement of the pawl member 152 between various positions causes the signal means to send a signal to notify the controller 210 that the sheet material has been removed. By way of example, such signal means can include an infrared emitter and detector that detects movement of the pawl member 152 between first and second positions, though any suitable sensor can be employed such as a proximity sensor or other detector, a magnetic switch, or a mechanical switch. After receiving a signal indicating removal of the sheet material, the control system 24 further can activate a paper detection sensor 158 (FIG. 4) to verify that the sheet material has been removed from the discharge chute. An example of such a mechanism is shown in U.S. patent application Ser. No. 13/155,528, the disclosure and figures of which is incorporated herein by reference herein as if set forth in their entirety.

In alternative constructions, the cutting mechanism can be configured to move or be actuated at a prescribed or preset point during a revolution of the feed roller 18, or after a prescribed rotation of the feed roller 18 so as to selectively cut or perforate the sheet material after a desired or prescribed length or portion of the sheet material has been fed or dispensed. For example, embodiments of the present disclosure described herein can utilize concepts disclosed in commonly-owned U.S. patent application Ser. Nos. 15/185, 937 and 15/848,643, the disclosure and figures of which are incorporated by reference herein as if set forth in their entireties.

Figure 3:
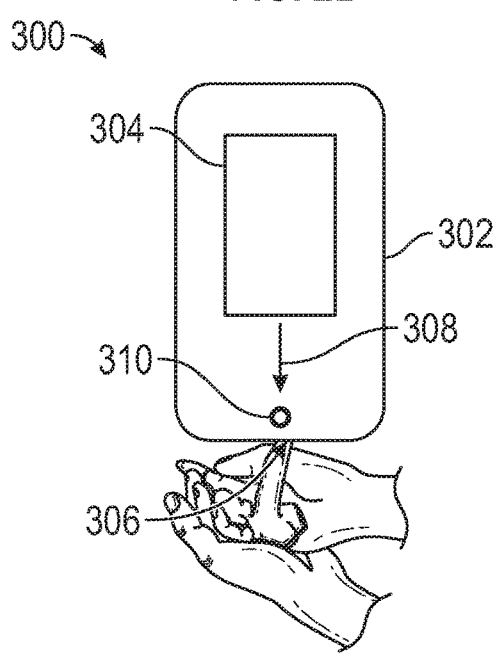
FIG. 3 shows a schematic diagram of a fluid dispenser according to one aspect of the present disclosure.

FIG. 3 shows a schematic diagram of a liquid or fluid dispenser 300 according to one embodiment of the present disclosure. The liquid dispenser 300 generally includes a dispenser housing 302 that supports/houses a supply chamber or reservoir 304 that contains/stores a liquid, e.g., liquid soap, hand sanitizer, etc. The liquid dispenser 300 further includes one or more nozzles or other suitable discharge outlet 306 for providing the liquid to the user, and the liquid dispenser includes a dispensing mechanism including a pumping system or mechanism 308, e.g., including one or more pumps or other suitable actuators, for directing or moving the liquid from the supply chamber 304 to the discharge outlet 306. The liquid dispenser 300 further includes one or more sensors 310, e.g., including an IR sensor, in communication with a controller, such as controller 510A/510B shown in FIGS. 8A-8B, that is configured to control operation of the pumping mechanism 308. The one or more sensors 310 can be configured as proximity sensors to gather information that is related to the presence of an object, such as a user's hand, near or proximate the dispenser 300. Accordingly, in operation, when a user places their hand in proximity to the one or more sensors 310, the one or more sensors 310 provide a signal to the controller to activate the pumping mechanism 308 for dispensing a select or prescribed amount of liquid. The controller further is coupled to a power source, e.g., one or more batteries or an AC power source, such as power source 514A/514B in FIG. 8A/8B to power the controller, dispensing mechanism 308, and the one or more sensors 310.

FIG. 4 illustrates a block diagram of an electronic control system or circuit 24 for operating the dispenser 10 in an exemplary embodiment. The dispenser assembly 10 or operative components thereof may be powered by a power supply 200, such as one or more batteries 202 contained in a battery compartment, though any suitable battery storage device may be used for this purpose. Alternatively, or in addition to battery power, the power supply 200 may also include a building's alternating current (AC) distribution system as indicated at 204. For this purpose, a plug-in modular transformer/adapter could be provided with the dispenser 10, which connects to a terminal or power jack port located, for example, in the bottom edge of the circuit housing for delivering power to the control system 24 and associated components. The control system 24 also may include a mechanical or electrical switch that can isolate the battery circuit upon connecting the AC adapter in order to protect and preserve the batteries.

In one example embodiment, the control system 24 can include or otherwise communication with a sensor 28, such as a proximity sensor or other detector 206, configured to capture information related to detect an object placed in a detection zone external to the dispenser to initiate operation of the dispenser, e.g., to detect a presence of a user or a user's hand within a prescribed zone, area or range of the sensor 28. This sensor 28 may be a passive infrared sensor that detects changes in ambient conditions, such as ambient light, capacitance changes caused by an object in a detection zone, and so forth. In an alternate embodiment, the sensor 28 may be an active device and include an active transmitter and associated receiver, such as one or more infrared (IR) transmitters and an IR receiver. The transmitter transmits an active signal in a transmission cone corresponding to the detection zone, and the receiver detects a threshold amount of the active signal reflected from an object placed into the detection zone. The control system 24 generally will be configured to be responsive to the sensor 28 for initiating a dispense cycle upon a valid detection signal therefrom. For example, the proximity sensor 206 or other detector can be used to detect both the presence of a user's hand. The dispenser 10 can additionally include a paper detector sensor 208, such as one or more infrared emitters and infrared detectors with one infrared emitter/detector, pair aligned to detect a user's hand below the dispenser 10 and the second infrared emitter/detector pair aligned to detect a sheet hanging below the outermost front edge of the discharge.

The controller 210 of the control system 24 can to control activation of the dispensing mechanism 74, e.g., upon valid detection of a user's hand by the sensor 28 for dispensing a measured length of the sheet material 12. In one embodiment, the controller 210 can track the running time of the drive motor 74 of the motorized feed roller, and/or receive feedback information directly therefrom indicative of a number of revolutions of the feed roller 18 and correspondingly, an amount of the sheet material feed thereby. In addition, or as a further alternative, sensors and associated circuitry may be provided for this purpose. Various types of sensors can include IR, radio frequency (RF), capacitive or other suitable sensors, and any one or a combination of such sensing systems can be used. The controller 210 also can control the length of sheet material dispensed. Any number of optical or mechanical devices may be used in this regard, such as, for example, an optical encoder may be used to count the revolutions of the drive or feed roller 18, with this count being used by the controller 210 to meter the desired length of the sheet material to be dispensed.

The processing logic for operation of the electronic dispenser in, for example, the hand sensor and butler modes, can be part of the control software 210C stored in the memory 210B of the controller 210 or other memories included in the control system 24. One or more binary flags are also stored in memory and represent an operational state of the dispenser (e.g., "paper cut" set or cleared). An operational mode switch in dispenser sets the mode of operation. In the hand sensor mode, the proximity (hand) sensor detects the presence of a user's hand below the dispenser 10 and in response, the motor 74 is operated to dispense a measured amount of sheet material 12. The controller 210 can then monitor when the sheet of material is removed. For example, actuation of the pawl member 152 or triggering/activation of a paper detection sensor 208 can determine the removal of paper and reset the hand sensor. The proximity sensor 206 also can be controlled to not allow additional sheet material to be dispensed until the proximity sensor is reset. If the proximity sensor 206 detects the presence of a user's hand but does not dispense sheet material, the controller 210 can check for sheet material using the paper detection sensor 208. If sheet material 12 has not been dispensed (i.e., no sheet material is hanging from the dispenser), the motor 74 will be activated to dispense a next sheet.

A multi-position switch 212 also can be provided to switch the dispenser operation between a first or standard operation mode and a second mode, such as a butler mode. In such butler mode, the proximity sensor 208 for detecting the presence of a user's hand/object can be deactivated, and the control system 24 can automatically dispense sheet material when the cover is closed and the dispenser is put into operation. The paper detection sensor 208 further can determine if a sheet is hanging from the dispenser. If sheet material is hanging, the control system 24 will then monitor when the sheet of material is removed. For example, a cutting mechanism movement detector, which may be arranged and configured to detect actuation or movement of the cutting mechanism; the pawl member; and/or the paper detection sensor can determine the removal of paper and reset the dispenser. The next sheet will be dispensed automatically. If the paper detection sensor 158 determines the absence of hanging sheet material, the motor 74 will be activated to dispense the next sheet. The control system 24 can then determine if the sheet has been removed before dispensing another sheet.

In one embodiment, the dispenser assembly 10 is operative in a first mode to be responsive to a signal from the proximity sensor to dispense a sheet of material. The dispensing mechanism is operative in a second mode to dispense a next sheet in response to the signal means being activated by movement of the cutting mechanism or tear bar to its extended position in response to dispensed sheet material 12 being removed from the dispenser. In another embodiment, the dispenser 10 can be operative in a second mode to dispense a next sheet in response to a signal means being activated by movement of the cutting mechanism, and a signal from a paper detection sensor 208 that the sheet material 10 has been removed from the dispenser. Such a sensor can be affixed to an external surface of the discharge rather than inside the discharge.

The dispenser 10 generally can dispense a measured length of the sheet material, which may be accomplished by various means, such as a timing circuit that actuates and stops the operation of the motor driving the feed roller after a predetermined time. In one embodiment, the drive motor 74 can provide direct feedback as to the number of revolutions of the feed roller 18, indicative of an amount of the sheet material 12 fed thereby. Alternatively, a motor revolution counter can be provided that measures the degree of rotation of the feed roller 18 and is interfaced with the controller 210 or other control circuitry to stop a drive roller motor after a defined number of revolutions of the feed roller 18. This counter may be an optical encoder type of device, or a mechanical device. The control system 24 may include a device to allow maintenance personnel to adjust the sheet length by increasing or decreasing the revolution counter set point. The multi-position switch 212 can also be in operable communication with the controller 210 to select one of a plurality of time periods as a delay between delivery of a first sheet and delivery of a next sheet to the user. Embodiments of the present disclosure described herein can also utilize concepts disclosed in commonly-owned U.S. Pat. No. 7,213,782 entitled "Intelligent Dispensing System" and U.S. Pat. No. 7,370,824 entitled "Intelligent Electronic Paper Dispenser," both of which are incorporated by reference in their entireties herein.

Figure 5:
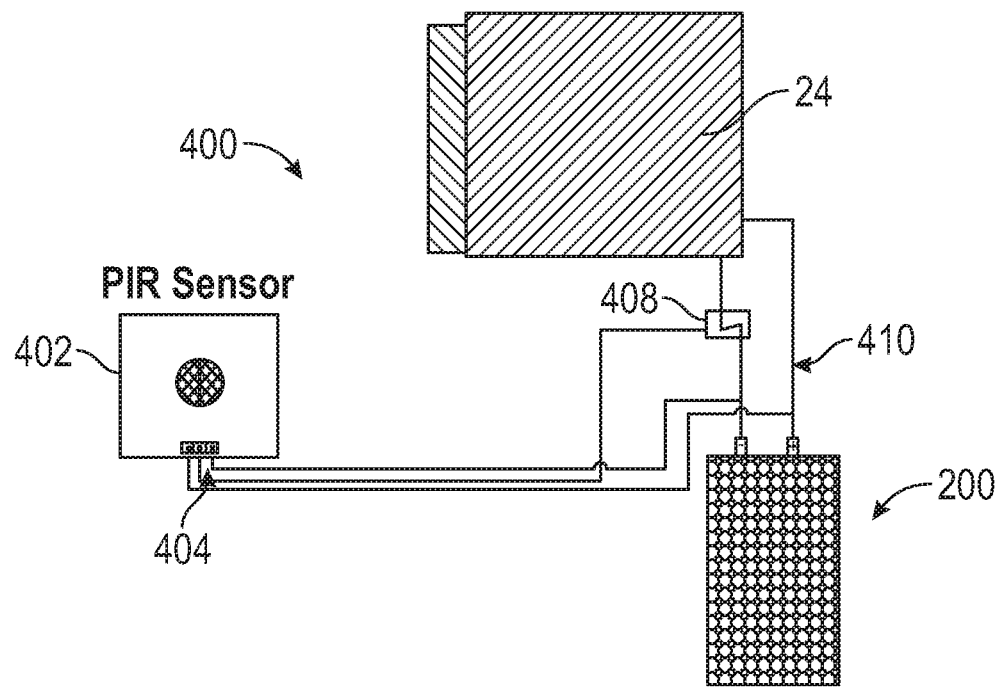
FIG. 5 shows a schematic view of a power management assembly according to one aspect of the present disclosure.
Figure 6:
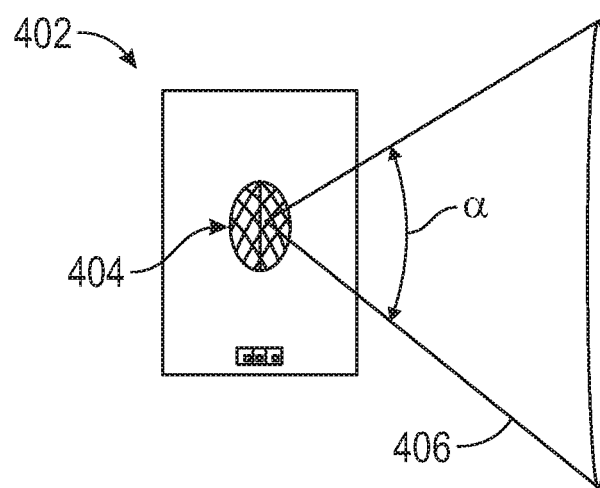
FIG. 6 shows a schematic view of an infrared radiation sensor of the power management assembly of FIG. 5.

As shown in FIGS. 5 and 6, the sheet material dispenser 10 or the fluid dispenser 300 also includes a power management assembly 400 that is configured to activate and deactivate the dispenser 10/300 based on a detected presence of a user within a prescribed area or zone around the dispenser 10/300. For example, the power management assembly 400 can include one or more sensors 402 that are configured to gather environmental information within the prescribed zone/area around the dispenser 10/300 to detect the presence of people/users as they enter and exit the area or zone where the dispenser is located, e.g., a restroom, hospital room, etc. For example, as further shown in FIGS. 4 and 5, the power management assembly 400 further can be integrated with or otherwise in communication with the dispenser's control system 24 to activate and deactivate the control system 24 based on the detected presence of people/users by the sensor(s) 402.

FIG. 6 shows that the one or more sensors 402 can include one or more passive infrared radiation ("PIR") sensor(s) 404 that are configured to detect infrared radiation of people/users, which is indicative of the presence or movement of the people/users within a prescribed detection range, area, zone, etc. 406 covered by the infrared radiation sensor 404. In one embodiment, as shown in FIG. 6, the detection area 406 of the one or more infrared radiation sensors 404 is generally conical with a detection range or angle α of about 110 degrees, though other suitable detection ranges/angles are possible, such as about 80 degrees, about 90 degrees, about 100 degrees, about 120 degrees, or more, without departing from the scope of the present disclosure.

Turning again to FIG. 5, the power management assembly 400 also can include a switch or switch circuitry 408, e.g., including a triode, or other suitable switching mechanism, that is coupled to a lead or other coupling/connector 410 connecting the power source 200 and the control system 24 of the dispenser. The switch 408 can be activated to connect and disconnect the control system 24 from the power source 200 (e.g., the switch 408 includes first, disconnected position where the control system 24 and the power source 200 are disconnected and the switch 408 includes a second, connected position wherein the control system 24 and the power source 200 are connected). In this regard, the switch 408 can couple the control system 24 to the power source 200 such that the control system 24 can draw or consume power from the power source 200, and the switch 408 can disconnect or decouple the control system 24 from the power source 200 (e.g., after a safe shutdown sequence of the controller 210) such that the control system 24 does not draw or consume power from the power source 200.

FIG. 5 further shows that the switch 408 can be connected to the infrared radiation sensor 404, such that the switch 408 can be activated to connect and disconnect the control system 24 and the power source 200 based on detection of or failure to detect a user/person. That is, the switch 408 is configured to couple and decouple the power source 200 and the control system 24 responsive to or based on signals received from the infrared radiation sensor 404. Thus, the switch 408 can decouple the power source 200 and the control system 24 when the PIR sensor 404 does not capture radiation of one or more persons or individuals (so that no power is consumed from the power source 200 by the control system 24 during such a non-operative state), and can re-engage or couple the power source 200 and the control system 24, so that the control system 24 can receive/draw power from the power source when the PIR sensor 404 captures radiation of one or more persons or individuals. The PIR sensor 404 remains connected to the power source 200 and consumes a minimal amount of power therefrom (FIG. 5).

In operation, the power management assembly 400 initially is in a low power mode or state, in which the control system 24 of the dispenser is deactivated (e.g., the switch 408 is in the first, disconnected or decoupled position in which the control system 24 is not connected to, i.e., not in communication with the power source 200). When a user/person enters the area or zone 406 covered by the PIR sensor 404, in response to a detection thereof, the power management assembly 500 can be switched to an active mode and activates the dispenser/the control system 24 to allow normal function thereof, such as by engaging the switch 408 to change from a first, disconnected state to its second, connected/coupled or operative state in which the control system 24 is connected to the power source 200). When no users are within the area or zone covered by the one or more PIR sensors 404, the power management assembly 400 returns dispenser back to a low or minimal power mode (e.g., once the detected users/people have left the area/zone covered by the infrared radiation sensor(s) 404, and/or after the selected period of no detected activity/presence, the switch 408 is returned its first, disconnected state again disconnecting the control system 24 from the power source 200).

In the low power mode or state, with the control system 24 disconnected, generally only the PIR sensor 404 will draw power from the power source 200. The PIR sensor 404 uses about one-tenth of power demands that the control system 24, e.g., the current use of the infrared radiation sensor can be about 50 µA (and in some embodiments as low as about 30 µA to about 10 µA), while the current of the control system 24 is about 500 µA. Accordingly, in some embodiments, the dispenser 10/300 can consume less than about 50 µA in the low power state; in other embodiments, the dispenser can consume less than about 30 µA in the low power state; and in further embodiments, the dispenser can consume less than about 15 µA in the low power state; and in even further embodiments, the dispenser can consume less than about 10 µA in the low power state.

In alternative embodiments, one or more components of the dispenser, e.g., proximity sensors, monitoring systems, dispensing mechanisms, etc. may still be connected to the power source and draw at least some power therefrom in the low power state, and thus, in those alternative embodiments, the dispenser can consume less than about 250 µA, less than about 200 µA, less than about 150 µA, or less than about 100 µA in the low power state.

According to the present disclosure, the term about can be understood to cover values in the range of ±0.5 µA, though about can reflect any suitable value range, such as ±0.1 µA, ±1 µA, or up to ±3 µA, or other value ranges as will be understood by those skilled in the art. In this regard, the power management system according to embodiments of the present disclosure helps to save significant power in comparison to typical steady state dispensing systems.

Figure 7:
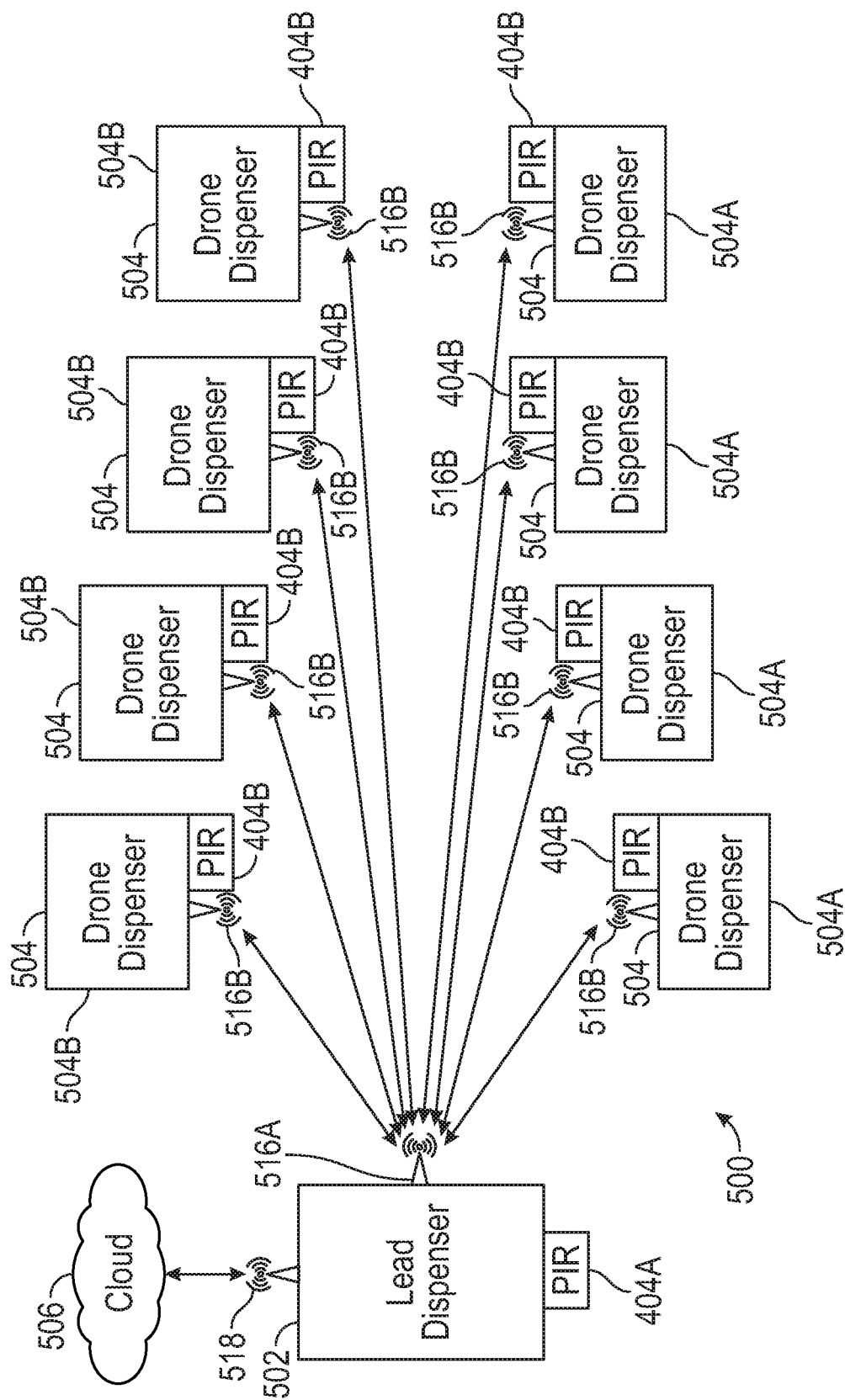
FIG. 7 shows a schematic view of a dispensing system including a lead dispenser and a plurality of drone dispensers according to principles of the present disclosure.

FIG. 7 shows an example embodiment of a dispensing system 500 according to principles of the present disclosure. The dispensing system 500 generally can include a dominant or lead dispenser 502 and a plurality of drone or follower dispensers 504 in communication with the lead dispenser 502. The plurality of drone dispensers 504 can include one or more liquid dispensers 504A, such as soap dispensers, hand sanitizer dispensers, etc. and/or one or more sheet material dispensers 504B, such as tissue dispensers, paper towel dispensers, etc. The lead dispenser 502 can include a sheet material dispenser (e.g., tissue dispensers, paper towel dispensers, etc.) or a liquid dispenser (e.g., a soap dispenser or a hand sanitizer dispenser).

The lead dispenser 502 further can be in communication with a network 506, such as cloud based network or other suitable public (e.g., the Internet) or private network, and the lead dispenser 502 can provide one or more signals, packets, etc. including, or otherwise related to, dispenser information and/or alerts, notifications, etc., generated by the lead dispenser 502 and the drone dispensers 504 to the network 506 for access by a system operator, maintained personnel, etc. The dispenser information can include information related to power levels (e.g., battery levels), supply levels (e.g., information related to remaining amounts of sheet material or liquid), usage (e.g., times and dates of when the dispenser was used, amounts the dispenser was activated during a specific time period, other usage rates or statistics, etc.) The alerts, notifications, etc. can be generated, e.g., if the dispensers 502/504 are experiencing a low power, low supply, error states, etc.

Figure 8A:
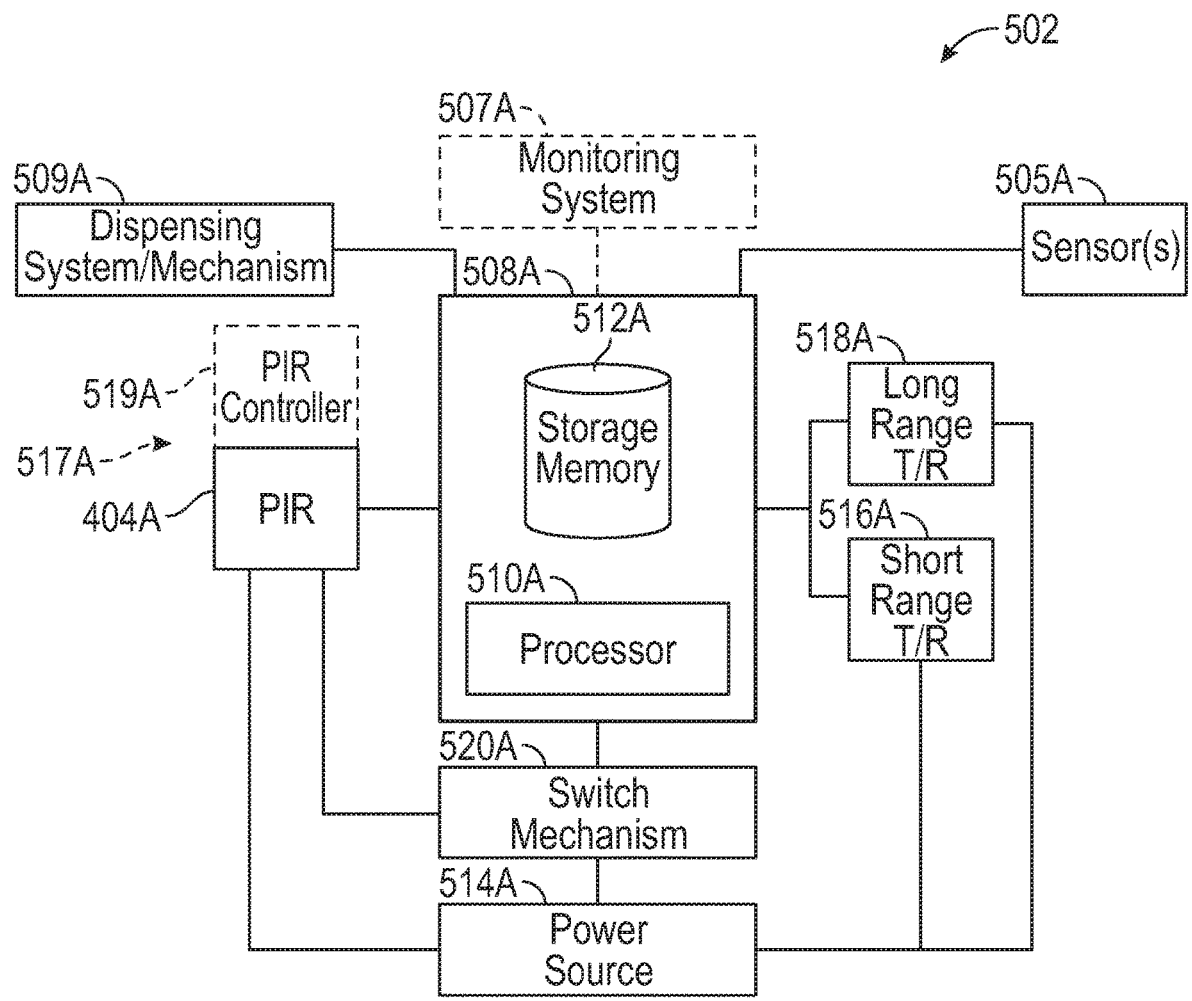
FIGS. 8A and 8B show schematic diagrams for a lead dispenser and a drone dispenser according to various aspects of the present disclosure.
Figure 8B:
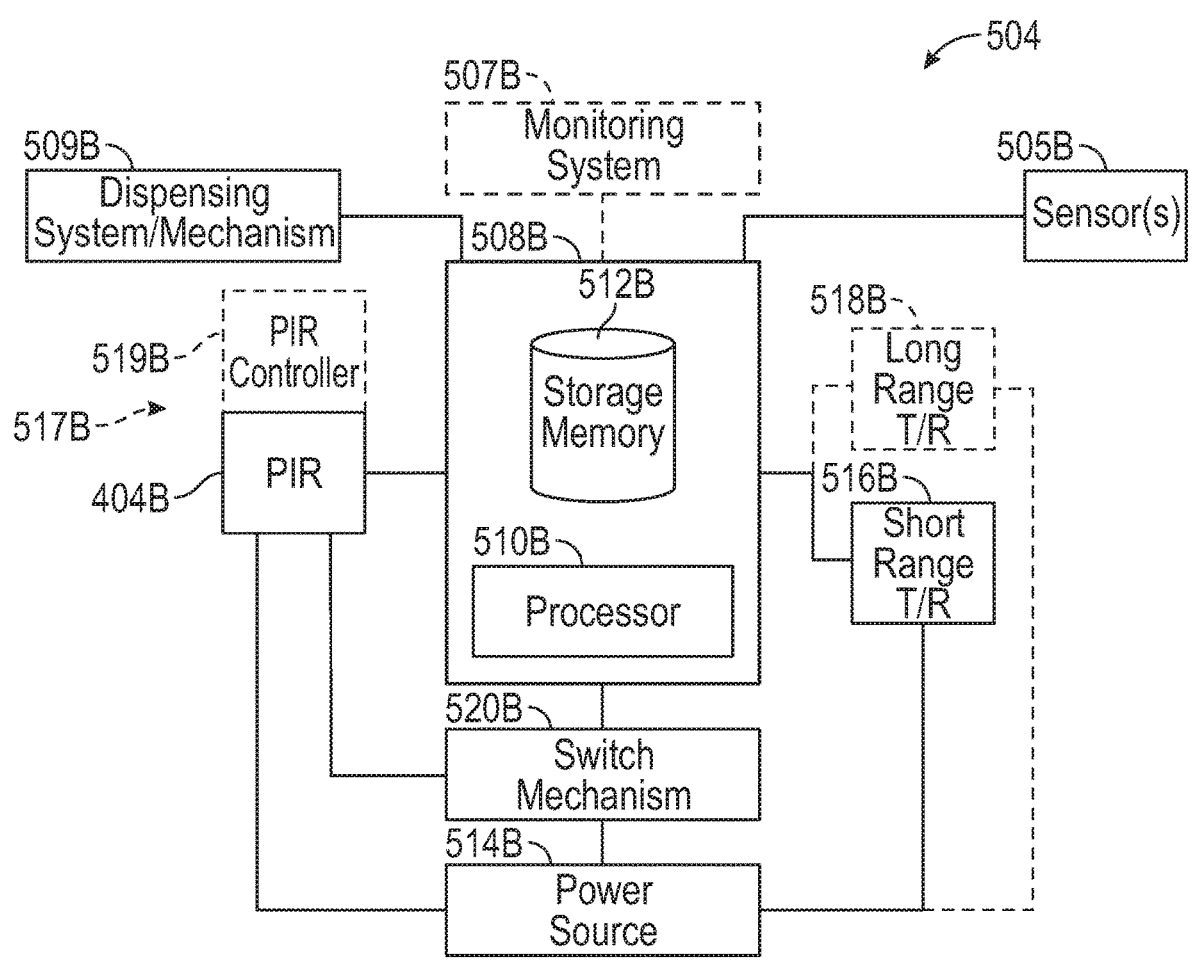

FIGS. 8A and 8B are schematic diagrams illustrating the lead dispenser 502 and drone dispensers 504, respectively. As shown in FIGS. 8A and 8B, the lead dispenser 502 and the drone dispensers 504 each include a dispenser controller or control unit 508A/508B that controls various operations/functions of the lead dispenser 502 and drone dispensers 504. Each dispenser controller 508A/508B of the dispensers 502/504 generally can include a printed circuit board assembly ("PCBA") with a processor 510A/510B, such as a micro-processor, CPU, etc., and one or more data stores or memories 512A/512B, such as RAM, ROM, or other non-volatile memories. Each dispenser controller 508A/508B further can be connected to or otherwise communicate with other components of the dispensers 502/504, such as sensors 505A/B, e.g., proximity sensors 28/310, paper detection sensors, personnel tracking sensors, etc.; optional monitoring systems 507A/B; drive systems or dispensing systems 509A/B, such as motor driven feed rollers 74, fluid pumps 308, etc.; or other suitable components of the dispensers 502/504.

The data stores 512A/512B can store instructions, workflows, etc. that can be accessed and executed by the processor 510A/510B to facilitate operations of the dispensers 502/504 (e.g., for dispensing of sheet material or liquid therefrom, for monitoring usage of the lead dispenser 502, such as operating a monitoring system 507A/B thereof that determines a remaining amount of sheet material or liquid, for communicating with and/or controlling the drone dispensers 504, etc.). The data stores 512A/512B further can store dispenser information generated by the respective dispensers 502/504, and one or more data stores 512A of the lead dispenser 502 can store dispenser information received from the drone dispensers 504.

In addition, as generally shown in FIGS. 8A and 8B, the lead dispenser 502 and drone dispensers 504 each include a power source 514A/514B, such as one or more batteries, an alternating current (AC) distribution system of a facility, or other AC or direct current (DC) power sources. The lead dispenser 502 and drone dispensers 504 will include a short-range receiver/transmitter 516A/516B, such as a Bluetooth® or other suitable RF or short-range signal receiver/transmitter, to facilitate communication between the lead dispenser 502 and the drone dispensers 504 (FIG. 7).

The lead dispenser 502 (FIG. 8A) also can include an additional, long-range receiver/transmitter 518A, such as a narrowband ("NB") receiver/transmitter (e.g., 4G, LTE, 5G, etc.) or other suitable transmitter/receiver, e.g., Wifi, for transmitting and/or receiving information to/from or otherwise communicating with the network 506 (FIG. 7). Further, in some variations, the drone dispensers 504 can have an identical construction to the lead dispenser 502 and will include a long-range receiver/transmitter 518B, such as a narrowband ("NB") receiver/transmitter (e.g., 4G, LTE, 5G, etc.) or other suitable transmitter/receiver, e.g., Wifi, etc. In these variations, the long-range transmitter/receivers 518B of one or more of the drone dispensers 504 can be deactivated or generally maintained in a low power state.

As further indicated in FIGS. 7-8B, the lead dispenser 502 and drone dispensers 504 each can include a passive infrared radiation (PIR) sensor 404A/404B configured to detect infrared radiation of a person or people (e.g., that is indicative of the presence or movement of individuals within a prescribed detection range, area, zone, etc. covered by each of the PIR sensors 404A/404B around their respective dispensers 502/504). PIR sensors 404A/404B can be in communication with the dispenser controller 508A/508B of their respective dispensers 502/504, which dispenser controller 508A/508B can be deactivated and activated based upon/responsive to signals received from corresponding PIR sensors 404A/404B (FIGS. 8A and 8B).

In particular, when the PIR sensors 404A/404B detect infrared radiation from a person or persons (e.g., indicating an occupied state or mode), their respective dispenser controllers 508A/508B and other dispenser components in communication therewith, such as sensors 505A/B, monitoring systems/sensors 507A/B, drive or pumping mechanisms 509A/B, etc., can be connected to or otherwise placed in communication with their corresponding power source 514A/514B so as to receive power/current therefrom. When the PIR sensors 404A/404B do not detect infrared radiation from a person or people (e.g., indicating an unoccupied state or mode), their respective dispenser controllers 508A/508B and other dispenser components in communication therewith can be placed in a low or minimal power state and disconnected from the power source 514A/514B such that no power/current is provided to the dispenser controller 508A/508B such that the dispenser controller 508A/508B and other dispenser components in communication therewith are deactivated and do not draw or consume power from the power source 514A/514B. That is, in the low or minimized power state, only the sensors 404A/404B will draw or consume power from the power source 514A/514B.

In one exemplary construction, as shown in FIGS. 8A and 8B, each of the lead dispenser 502 and drone dispensers 504 also can include a switch mechanism or circuitry 520A/520B, e.g., including an NPN triode or other, similar mechanism that can block or shut off power to the dispenser controllers 508A/508B. The switch mechanism 520A/520B will be in communication with the sensors 404A/404B to disconnect and connect the dispenser controller 508A/508B (and other dispenser components in communication therewith) from/to the power source 514A/514B in the unoccupied and occupied modes, respectively. For example, in the unoccupied mode (e.g., when the sensor 404A/404B does not detect infrared information from a person or people), the sensors 404A/404B can output one or more signals, e.g., a low level signal, to their respective dispenser controllers 508A/508B. Upon receipt of this low level signal, the dispenser controllers 508A/508B, e.g., the processor 510A/510B, can determine that the sensors 404A/404B are in the unoccupied mode, and the dispenser controllers 508A/508B can initiate a shutdown or power down sequence. In some embodiments, the switch mechanisms 520A/520B can be incorporated with the PCB of their associated dispenser controller 508A/508B; though the switch mechanisms 520A/520B otherwise be connected to or in communication with their dispenser controllers 508A/508B.

In some aspects, the dispenser controllers 508A/508B (and other dispenser components in communication therewith) can finish or complete any on-going work, functions, operations, etc. thereof and generate and transmit one or more command signals to place the short-range transmitter/receivers 516A/516B (as well as the long-range transmitter/receiver 518) into a low power/power off state. As the dispenser controller 508A/508B enters into its power down sequence, the dispenser controller 508A/508B can generate and output one or more signals, e.g., a low level signal, to the switch circuitry 520A/520B such that the switch circuitry 520A/520B is in an open or "off" state, disconnecting the power sources 514A/514B from their associated dispenser controllers 508A/508B to completely shut down/power off the dispenser controllers 508A/508B and substantially all other components of the dispensers 502/504, except for the sensors 404A/404B, and, in some variations, the short-range 516A/516B and long-range 518A/518B transmitter/receivers. In these variations, the transmitters/receivers 516A/516B and 518A/518B can be placed in a low power or sleep state. In this regard, the dispenser controller 508A/508B and substantially all other components of the dispensers 502/504 (e.g., sensors 505A/B, optional monitoring systems 507A/B, dispensing systems 509A/B, etc.) generally are decoupled from the power sources 514A/514B such that the dispenser controllers 508A/508B and other operative components of the dispensers 502/504 do not consume or draw power from the power sources 514A/514B while in such low/minimal power state.

The dispenser controllers 508A/508B can be powered on when their respective sensors 404A/404B capture infrared radiation from a person or persons and are in the occupied state. In particular, when one of the sensors 404A/404B captures infrared radiation of a person or persons to indicate an occupied mode, that sensor 404A/404B will output one or more signals, e.g., a high level signal, to its corresponding or associated switch circuitry 520A/520B to place such switch circuitry 520A/520B in a closed or "on" state to couple or re-establish communication between the power source(s) 519A/B and the dispenser controllers, and thus provide power to the dispenser controllers 508A/508B from the power source 514A/514B to place the dispenser controllers in an operative state for enabling dispensing operations. In addition, the dispenser controllers 508A/508B further can generate and provide one or more signals to activate or wake up the short-range transmitter/receivers 516A/516B and/or long-range transmitter/receivers 518A/518B, e.g., as needed, when powered on.

In some variations, a timer, time clock, timing circuit, etc. can be integrated with one or more of the sensors 404A/404B to delay the shutdown sequence of the dispenser controllers 508A/508B. For example, when the sensors 404A/404B do not detect the presence of a person, the timer can be activated, and upon expiration of the timer, the sensors 404A/404B can transmit the signals to their respective dispenser controller 508A/508B to initiate their power down sequence. The timer can be set to any suitable time period, such as about 30 seconds, about 1 minute, about 5 minutes, about 10 minutes or other suitable time periods.

Additionally, in some embodiments, the lead and/or drone dispensers 502 and 504 optionally can include a smart PIR sensor 517A/517B. The smart PIR sensor of the lead and/or drone dispensers can include a PIR controller 519A/519B, such as a mini-CPU or low power CPU or any other suitable computing or processing unit than consumes or draws minimal power (e.g., between about 20 µA to about 25 µA and as low as about 10 µA), that is integrated with or otherwise in communication with the PIR sensors 404A and 404B. In one embodiment, the PIR controllers 519A/B and the PIR sensors 404A/404B can be part of a printed circuit board assembly ("PCBA"); though the PIR controller 519A/B and the PIR sensors 404A/404B can be otherwise electrically connected or otherwise in communication without departing from the scope of the present disclosure.

The PIR controllers 519A/519B further can be in communication with the switch mechanisms 520A/520B and/or the dispenser controllers 508A/508B, and can generate one or more signals responsive to captured or detected radiation of the PIR sensors 404A/404B (i.e., depending on whether such PIR sensors 404A/404B are in an occupied or unoccupied state). That is, when each PIR controller 519A/519B determines that its corresponding PIR sensor 404A/404B does not capture radiation, i.e., is in the unoccupied state, each PIR controller 519A/519B can transmit one or more signals to its corresponding dispenser controller 508A/508B and/or switch mechanism 520A/520B to place the dispenser 502/504 in the low or minimal power state, and when each PIR controller 519A/519B determines that its corresponding PIR sensor 404A/404B captures infrared radiation, the PIR controller 519A/519B can generate and transmit one or more signals to its corresponding switch mechanism 520A/520B and/or dispenser controller 508A/508B to place the dispenser 502/504 to place the dispenser 502/504 in the "on" or full power state.

In particular, according to one embodiment, when the PIR sensors 404A/404B detect the presence of one or more individuals, the PIR controllers 519A/519B will receive one or more high level signals from their PIR sensors 404A/404B. Upon receipt of these high level signal(s), the PIR controllers 519A/519B will output one or more high level signals to their corresponding dispenser controllers 508A/508B and/or the switch mechanisms 520A/B for powering on the dispenser controllers 508A/508B. Furthermore, when the PIR sensors 404A/404B do not detect the presence of any individuals, the PIR controllers 519A/519B will receive one or more low level signals from the PIR sensors 404A/404B. Upon receipt of these low level signal(s), the PIR controllers 519A/519B will output one or more low level signals to the dispenser controllers 508A/508B to initiate a shutdown sequence and allow the dispenser controllers 508A/508B to finish any ongoing work/processes or other work/processes as necessary. When the work/processes of the dispenser controllers 508A/508B are complete, the dispenser controllers 508A/508B can output one or more low level signals to indicate that its work is complete, and thereafter the PIR controllers 519A/519B can output one or more signals to deactivate the dispenser controllers 508A/508B (e.g., the PIR controllers 519A/519B can output one or more signals to the switch mechanisms 520A/520B to decouple/disconnect the dispenser controllers 508A/508B and the power sources 514A/514B or the PIR controllers 519A/519B can output one or more signals to the dispenser controllers 508A/508B to disconnect/decouple the dispenser controllers 508A/508B and the power sources 404A/B or to otherwise deactivate/power down the dispenser controllers 508A/508B). That is, the dispenser controllers 508A/508B generally remain coupled to their corresponding power sources 514A/514B or activated until the PIR controllers 519A/B receives the low level signal(s) therefrom to indicate that necessary work is complete and the dispenser controllers 508A/508B can be safely decoupled from power or otherwise deactivated. The PIR controllers 519A/519B further can output one or more high level signals to help to insure stability of the dispenser controllers 508A/508B.

In some variations, each PIR controller 519A/519B can include one or more timers, which can be initiated after the PIR controllers 519A/519B are initially placed in their unoccupied state. Thereafter, until the expiration of the timer(s), the PIR controller 519A/519B will not decouple the dispenser controllers 508A/508B from the power source 514A/514B or otherwise deactivate the dispenser controller 508A/508B. Such timers can be set at varying time intervals (e.g., based on time of day/usage period, usage history, or other factors) to help reduce unnecessary cycling power off/power on cycles). For example, during peak usage times, a longer timer can be used before shut down/powering down of the dispensers, while at night, when usage is lower, a shorter timer period can be used.

In alternative constructions, the switch mechanism 520A/520B can be omitted, and when the PIR sensor 404A/404B is determined to be in the unoccupied state, the PIR controller 519A/519B can generate one or more signals to the dispenser controller 508A/508B to initiate a shutdown or power down sequence, such that the dispenser controller 508A/508B and other operative dispenser components in communication therewith shut down/shut off and consume minimal or no power from the power source 514A/514B. Then, when the PIR sensor 404A/404B is in the occupied state, i.e., captures infrared radiation, the PIR controller 518A/519B can transmit one or more control signals to the dispenser controller 508A/50B to initiate a start-up sequence of the dispenser controller 508A/508B.

The PIR controller 519A/519B can consume between less than about 25 µA to less than about 10 µA, e.g., in one embodiment, less than about 12 µA, while the PIR sensor 404A/404B can consume between less than about 20 µA to less than about 10 µA, e.g., in one embodiment, less than about 12 µA. Accordingly, with embodiments of the present disclosure, in the low/minimal power state, the dispensers 502/504 can consume less than about 45 µA, less than about 44 µA, less than about 43 µA, less than about 42 µA, less than about 41 µA, less than about 40 µA, less than about 39 µA, less than about 38 µA, less than about 37 µA, less than about 36 µA, less than about 35 µA, less than about 34 µA, less than about 33 µA, less than about 32 µA, less than about 31 µA, or less than about 30 µA, less than about 29 µA, less than about 28 µA, less than about 27 µA, less than about 26 µA, less than about 25 µA, less than about 24 µA, less than about 23 µA, less than about 22 µA, less than about 21 µA, and/or less than about 20 µA, or lower amounts without departing from the scope of the present disclosure.

In addition, upon activation of the lead dispenser 502 and/or the drone dispensers 504, e.g., when the sensors 404A/404B of the dispensers 502/504 are in the occupied state, the dispenser controllers 508A/508B of the dispensers 502/504 can be activated (i.e., connected to the power source 514A/514B), and may log, generate, and store dispenser information related to operations/functions of the dispensers 502/504. For example, the lead 502 and drone dispensers 504 can generate dispenser information, e.g., including time and date information, when the dispensers 502/504 are activated, and can store the dispenser information in the one or more data stores 512. The lead dispenser 502 and drone dispensers 504 further can generate, record, etc., additional dispenser information, such as voltage usage, power levels, paper or liquid levels, usage statistics, etc. and/or other suitable dispenser information, which also can be stored in the data store(s) 512.

The drone dispensers 502 generally transmit the dispenser information to the lead dispenser 502 each time the drone dispensers 504 are activated (i.e., each time the sensor 404 of the drone dispensers is in the occupied stated); however, in the alternative, the drone dispensers 504 can provide the dispenser information to the lead dispenser 504 periodically, e.g., the drone dispensers 504 can provide the dispenser information to the lead dispenser 504 after a prescribed number of activations, e.g., every five, ten, twenty, fifty, etc., activations, or the drone dispensers 504 can provide the dispenser information after a certain time period, a certain time in the day, etc.

The lead dispenser 502 stores the dispenser information received from the drone dispensers 504 (and generated by the lead dispenser 502) in the data stores 512A, and transmits signals, packets, etc., including or related to the dispenser information to the network 506. The lead dispenser 502 may transmit signals/packets including the dispenser information each time the lead dispenser 502 is activated (e.g., when the sensor 404A is in an occupied state). However, alternatively, the lead dispenser 502 can transmit the signals/packets including the dispenser information to the network 506 periodically, such as after a certain number of activations of the sensor 404, e.g., ten, twenty, thirty, forty or more activations thereof, though the lead dispenser 502 also can transmit the signals/packets including the dispenser information after a certain time period, a certain time in the day, etc. without departing from the present disclosure.

The dispenser information provided to the network 506 can be accessed by system operators, maintenance personnel, etc. and further can be processed, e.g., for tracking or mapping the movements of individuals throughout a facility including the dispenser system 500, for optimizing usage of the lead dispenser 502 and/or the drone dispensers 504, for maintenance or servicing of the lead dispenser 502 and/or the drone dispensers 504, etc.

The drone dispensers 504 further can generate and transmit alerts, notifications, etc., to the lead dispenser 502. For example, if one of the drone dispensers 504 is running low on sheet material or a liquid supply (e.g., as determined by one or more monitoring systems of the drone dispensers 504), is experiencing an error condition, such as a jam, component failure, etc., the drone dispenser 504 can generate and transmit and an alert to the lead dispenser 502 (i.e., using the short-range transmitter/receiver 516B). Upon receipt of the alert, the lead dispenser 502 may generate and transmit one or more signals or information packets including information related to the alert to the network 506 (using the long-range transmitter/receiver 518A/518B) to notify a system operator, maintenance provider, etc. of the alert e.g., so they can refill, replace the batteries, or otherwise service the drone dispenser 504.

The lead dispenser 502 further can generate and transmit alerts, notifications, etc. to the network (e.g., if the lead dispensers 502 is running low on sheet material or liquid supply, such as determined by one or more monitoring systems of the lead dispenser 502; is experiencing an error condition, such as a jam or a component failure; etc.). The alerts, notifications, etc. generally can be sent to the lead dispenser 502 and to the network 506 immediately or soon after the condition that led to generation of the alert, notification, etc.

The drone dispensers 504 further can continuously generate and transmit signals to the lead dispenser 502 when the sensors 404B of one or more of the drone dispensers 404 are in the occupied mode. For example, the drone dispensers 504 can transmit one or more signals, using the short range transmitter 516B thereof, to the lead dispenser 502 at a prescribed interval, e.g., about every 1 second, about every 10 seconds, about every 30 seconds, etc., when in the sensor 404B is in the occupied mode.

According to the present disclosure, the lead dispenser 502 generally remains in the on/active/full power state (i.e., with the dispenser controller 508A/508B and other dispenser components in communication therewith connected to/coupled with the power source 514A/514B) when one or more of the sensors 404B of one or more of the drone dispensers 504 are in an occupied state. That is, the lead dispenser 502 remains in the on state when signals are received from one or more of the drone dispensers 504 even if the sensor 404A of the lead dispenser 504 is in the unoccupied mode. Furthermore, the lead dispenser 502 can remain in the active/on state (i.e., with the dispenser controller 508A connected to/couple with the power source 514A) for a prescribed time period after the sensor 404A of the lead dispenser 502A and all of the sensors 404B of the drone dispensers 504 are in an unoccupied state (e.g., when no one is within a prescribed proximity to the lead 502 or drone 504 dispensers).

The prescribed time period can be set by the operator of the system and can include, but is not limited to, approximately five minutes, approximately ten minutes, approximately thirty minutes, approximately one hour, etc. or other suitable time period without departing from the scope of the present disclosure. Accordingly, when the dispenser controller 508A of the lead dispenser 502 determines that all of the sensors 404B of the corresponding drone dispensers 504 are in the unoccupied mode (e.g., when the short-range transmitter 516A of the lead dispenser fails to receive signals from the drone dispensers 502) and the sensor 404A of the lead dispenser 502 also is in an unoccupied mode, the dispenser controller 508A may initiate a timer, and upon expiration of the timer, the dispenser controller 508A can initiate the dispenser controller 508A power down sequence described above.

In some variations, the lead dispenser 502 can generate and transmit one or more signals to activate one or more of the plurality of drone dispensers 504 upon activation of the lead dispenser 502, e.g., when the sensor 404 of the lead dispenser 502 is in an occupied mode; however, all of the drone dispensers 504 can remain off/deactivated until their sensor 404B is in the occupied mode, without departing from the scope of the present disclosure. Furthermore, in some variations, the sensors 404B of the drone dispensers 504 can be disconnected from the power source 514B when the lead dispenser 502 is in the power down mode (and can be powered on when the transmitter/receiver 516B receives one or more signals from the lead dispenser 502).

In addition, in some variations, the lead dispenser 502 can be activated when a signal is received by the long-range transmitter/receiver 518A/518B, e.g., when a system operator, maintenance personnel, etc., want to access the dispenser information of the lead dispenser 502 or one or more of the drone dispensers 504. The lead dispenser 502 further can be activated when a signal is received from one or more of the drone dispensers 504, e.g., via the short-range transmitter 516A (or in the long-range transmitter in the case one is included with one or more of the drone dispensers 504.

Figure 9A:
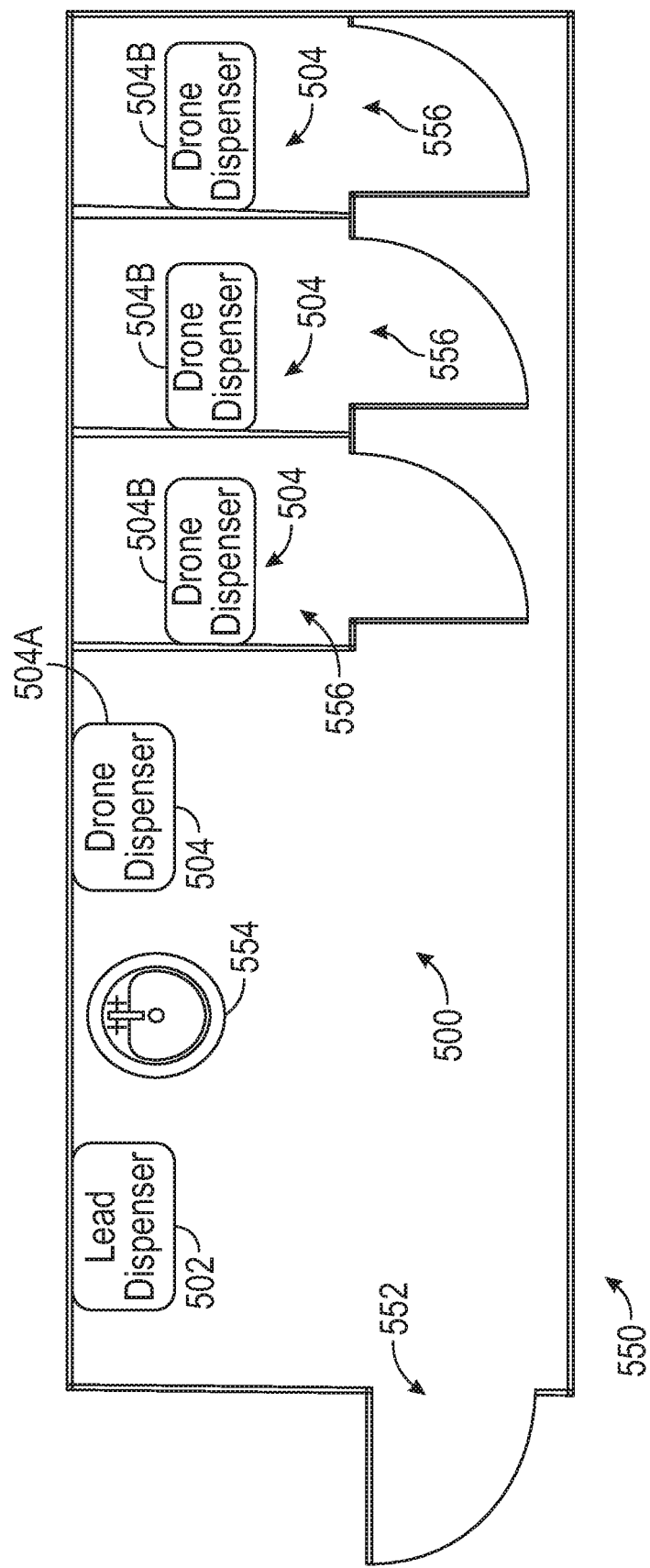
FIGS. 9A and 9B show exemplary facilities including a dispensing system such as illustrated in FIG. 7.
Figure 9B:
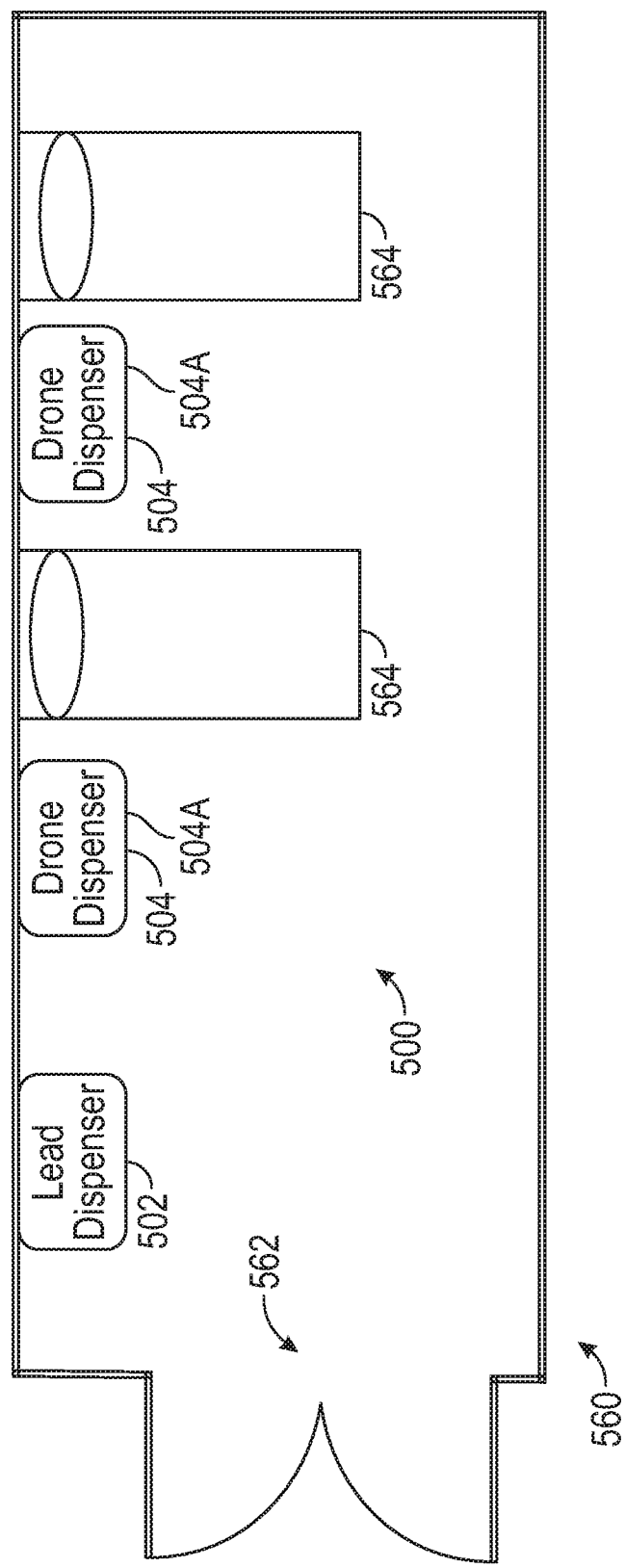

As generally shown in FIGS. 9A and 9B, the dispensing system 500, including a lead dispenser 502 and a plurality of drone dispensers 502 can be placed at various locations within a facility, such as within a restroom 550 of the facility (FIG. 9A), or within hospital rooms 560 (FIG. 9B).

By way of example, and as shown in FIG. 9A, a lead dispenser 502, which can include a sheet material dispenser, can be placed at, near, or substantially proximate to an entry 552 to a restroom 550 (e.g., such that the sensor 404A of the lead dispenser 502 is in the occupied mode when a person or persons enter the restroom 550). The plurality of drone dispensers 504 can include a liquid dispenser 504A positioned substantially near a sink or faucet 554 of the restroom 500, and further can include a plurality of tissue dispensers 504B placed within the various stalls 556 of the restroom 550.

The lead dispenser 502 can be activated when an individual(s) enters the restroom 550, and the tissue dispensers 504B further can be activated and generate and transmit one or more signals to the lead dispenser 502 when the individual enters one of the stalls 556. When the individual exits the stall 556, the tissue dispenser 504B can be deactivated. The liquid dispenser 504A can be activated when the individual approaches the sink 554, e.g., to wash their hands or to user the liquid dispenser 504A, and deactivated after the individual moves sufficiently away from the liquid dispenser 504A. If the liquid dispenser 504A and/or the tissue dispensers 504B are running low on paper, have a low power supply, or are experiencing an error condition, the dispensers 504A/504B can generate and transmit an alert, notification, etc. to the lead dispenser 502 to be transmitted to the network 506 to notify system operators, maintenance personal, etc.

The lead dispenser 502 generally can remain activated while an individual is in the restroom 550, with the lead dispenser 502 receiving signals from the tissue 504B and/or liquid dispensers 504B. The lead dispenser 502 further can receive dispenser information from the dispensers 504A/504B related to the movements/activities of the individual (e.g., the particular dispensers activated and/or used and the time and date when they were used) and provide that dispenser information as well as any dispenser information generated by the lead dispenser 502 to the network 506 for processing, e.g., to track or map movements of the individual in the restroom, activities of the individual within the restroom (e.g., to determine if the individual washed their hands after using a stall), etc.

After the individual exits the restroom and no other individuals or activity are detected in the restroom, the lead dispenser 502 can be deactivated, i.e., its dispenser controller 508A and dispenser components in communication therewith can be disconnected from the power source 514A, as can be the drone dispensers 504 linked thereto. As a result, when the restroom 550 is unoccupied, the power consumed by the dispenser system 500 in the restroom 550 is substantially reduced, e.g., with the dispenser controller 508A/508B and substantially all other operative components of the dispensers 502/504 disconnected from the power sources 514A/514B, except for the sensors 404A and 404B and the long-range 518A and short-range receivers 516A and 516B, which remain active and in a low power or sleep state.

As shown in FIG. 9B, the dispenser system 500 also can be integrated within a hospital room 560. For example, the lead dispenser 502 can include a sheet material dispenser or a liquid (e.g., hand sanitizer) or other type dispenser positioned to be substantially adjacent, proximate, etc. an entry 562 of the hospital room 560 or otherwise positioned, arranged, oriented, etc. so that the sensor 404A of the lead dispenser 502 is in the occupied mode when a person or persons enter the hospital room 560. The drone dispensers 504 can include liquid dispensers 504A, such as soap or sanitation dispensers, positioned about the hospital room 560, or other type dispensers. For example, the drone dispenser 504 can be position to be substantially adjacent, proximate, or otherwise near a hospital bed 564 in the hospital room 560.

Accordingly, when one or more individuals enter the hospital room 560 the lead dispenser 502 can be activated (e.g., with the sensor 404A in the occupied mode, the dispenser controller 508A of the lead dispenser 502 can be connected to the power source 514A). In addition, the drone dispensers 504 can be activated when individuals in the hospital room 560 are within a certain proximity of the drone dispensers 504, e.g., as/when the individuals approach the hospital beds 564 and/or the dispensers 504. The lead dispenser 502 and the drone dispensers 504 further can generate, log, store, etc. dispenser information (e.g., times and dates of when the dispensers 502/504 where activated, whether the individuals used the dispensers 502/504, etc.). The drone dispensers 504 can transmit dispenser information and/or one or more alerts, notifications, etc. (e.g., if a lower power, low supply, error, etc., state is detected), and the lead dispenser 502 can transmit dispenser information/alerts received from the drone dispensers 504 and generated by the lead dispenser 502 to the network 506 for processing thereof, e.g., for tracking usage of the dispensers 502/504, for maintenance of the dispensers 502/504, and/or for tracking or mapping movements or other activities of the individuals within the hospital room 560, etc.

When the sensors 404B of the drone dispensers 504 are in the unoccupied state, the drone dispensers 504 are placed in the low/minimal power state (i.e., with the power source 514B disconnected from the dispenser controller 508B and other operative dispenser components in communication therewith). And, when all of the sensors 404A and 404B of the lead dispenser 502 and the drone dispensers 504 are in the unoccupied state, the lead dispenser 502 is placed in the low/minimal power state (i.e., with the power source 514A disconnected from the dispenser controller 508A and other operative dispenser components in communication therewith) after a prescribed time period, such as approximately 5 minutes, approximately 10 minutes, etc. As a result, when the hospital room 560 is unoccupied, the power consumed by the dispenser system 500 in the hospital room is substantially reduced, e.g., with the dispenser controller 508A/508B and substantially all other power consuming components of the dispensers 502/504 being disconnected from the power sources 514A/514B, except for the sensors 404A and 404B and the long-range 518A and short-range receivers 516A and 516B in a low power or sleep state.

In addition, or in alternative constructions, the lead dispenser 502 and the drone dispensers 504 (e.g., the liquid dispenser 504A shown in FIG. 9B) further can communicate with devices, such as badges, fobs, key cards, etc. or other passive or active devices, carried by hospital personnel. For example, the short-range transmitters/receivers 516A/516B of the lead dispenser 502 and the drone dispensers 504 (or additional receiver/transmitters incorporated or otherwise in communication with lead dispenser 502 and the drone dispensers 504) can send and/or receive one or more signals to the devices carried by the hospital personnel. The lead dispenser 502 and drone dispensers 504 further can generate, log, store, etc. device information based on the signals transmitted to or received from the carried devices. The drone dispensers 504 further can transmit the generate/stored device information to the lead dispenser 502, and the lead dispenser can transmit the device information to the network 506 for processing thereof, e.g., for tracking or mapping activities or movements of the hospital personnel carrying the devices, for monitoring compliance with sanitation procedures, etc.

Exemplary processes and systems for mapping/tracking individuals are discussed in U.S. Pat. Nos. 9,741,233, 9,972,193, 10,446,013, which is specifically incorporated by reference herein as if set forth in its entirety.

The foregoing description generally illustrates and describes various embodiments of the present invention. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of the present invention. Accordingly, various features and characteristics of the present invention as discussed herein may be selectively interchanged and applied to other illustrated and non-illustrated embodiments of the invention, and numerous variations, modifications, and additions further can be made thereto without departing from the spirit and scope of the present invention as set forth in the appended claims.

What is claimed is:

1. A dispenser, comprising:
a supply of liquid or sheet material;
a dispenser housing in which the supply is received;
a dispensing mechanism located within the dispenser housing in communication with the supply and configured to dispense prescribed amounts of the supply from the dispenser housing;
a proximity sensor positioned along the dispenser housing and configured to detect a presence of a user proximate the dispenser;
a controller in communication with the dispensing mechanism and the proximity sensor, the controller configured to activate the dispensing mechanism to dispense the prescribed amounts of the supply upon receipt of one or more signals from the proximity sensor indicative of the presence of the user proximate the dispenser;
a power source supplying power to the controller, dispensing mechanism and proximity sensor; and
a power management system in communication with the controller and comprising a passive infrared radiation sensor arranged along the dispenser housing and configured to detect infrared radiation emitted by one or more users within a prescribed detection range, area, or zone of the dispenser, and a switching mechanism arranged between the power source and the controller and in communication with the passive infrared sensor;
wherein, when the passive infrared radiation sensor does not capture infrared radiation within the prescribed detection range, area, or zone, the dispenser is placed in a low power state with the passive infrared sensor remaining connected to the power source and the controller, and the switching mechanism is operated so as to disconnect the controller, the dispensing mechanism, and the proximity sensor from the power source; and
wherein, when the passive infrared radiation sensor captures infrared radiation within the prescribed detection range, area, or zone, the switching mechanism of the power management system is operated to connect the controller, the dispensing mechanism, and the proximity sensor to the power source.

2. The dispenser of claim 1, further comprising a passive infrared radiation sensor controller that is integrated with the passive infrared radiation sensor, the passive infrared radiation sensor controller being configured to generate one or more signals responsive to signals from the passive infrared radiation sensor to connect and disconnect the controller, the dispensing mechanism, and/or the proximity sensor to and from the power source.

3. The dispenser of claim 1, wherein:
when the passive infrared radiation sensor does not capture infrared radiation within the prescribed detection range, area, or zone, the passive infrared radiation sensor outputs one or more low level signals to the controller,
upon receipt of the one or more low level signals from the passive infrared radiation sensor at the controller, the controller initiates a shutdown sequence to complete any ongoing work, functions, or operations of the controller, and
upon completion of the shutdown sequence, the controller outputs one or more signals to the switching mechanism such that the switching mechanism decouples the power source and the controller, proximity sensor, and/or the dispensing mechanism.

4. The dispenser of claim 1, wherein the dispenser consumes less than about 100 µA in the low power state.

5. The dispenser of claim 1, wherein the dispenser consumes less than about 50 µA in the low power state.

6. The dispenser of claim 1, wherein the dispenser consumes less than about 20 µA in the low power state.

7. The dispenser of claim 1, further comprising a timer integrated with the passive infrared radiation sensor, wherein the timer is activated when the passive infrared radiation sensor does not detect infrared radiation within the prescribed detection range, area, or zone, and wherein upon expiration of the timer, the power source is disconnected from the controller, proximity sensor, and/or the dispensing mechanism.

8. The dispenser of claim 1, wherein the dispensing mechanism includes a feed roller that is configured engage and move sheet material from the supply of sheet along a discharge path and out of the dispenser for dispensing thereof.

9. The dispenser of claim 1, wherein the supply of liquid includes a supply chamber that stores a liquid; and wherein the dispensing mechanism includes a pump that directs the liquid from the supply chamber to a discharge.

10. A dispensing system, comprising:
a lead dispenser including a lead dispenser controller for controlling one or more operations of the lead dispenser, and at least one passive infrared radiation sensor in communication with the lead dispenser controller, the passive infrared radiation sensor configured to capture infrared radiation indicative of one or more individuals present within a prescribed detection range, area, or zone of the lead dispenser; and
a plurality of drone dispensers each configured to communicate information to the lead dispenser, and each including a drone dispenser controller for controlling one or more operations of each drone dispenser, at least one a passive infrared radiation sensor in communication with the drone dispenser controller of each drone dispenser
wherein each of the drone dispensers is connected to a power source configured to supply power to the drone dispenser;
wherein the passive infrared radiation sensor of each drone dispenser is configured to capture infrared radiation indicative of one or more individuals present within a prescribed detection range, area, or zone of each drone dispenser, and wherein when the passive infrared radiation sensor of one of the drone dispensers does not capture infrared radiation, the drone dispenser controller, and a dispensing mechanism and a proximity sensor connected to the drone dispenser controller of that drone dispenser are disconnected from the power source connected thereto; and
a network in communication with the lead dispenser, the lead dispenser communicating information related to the lead dispenser and the information received from the plurality of drone dispensers to the network.

11. The dispensing system of claim 10, wherein a power source of the lead dispenser remains connected to the lead dispenser controller of the lead dispenser when the at least one passive infrared radiation sensor of the lead dispenser or the at least one passive infrared sensor of any of the plurality of drone dispensers capture infrared radiation indicative of one or more individuals present within the prescribed range, area or zone thereof.

12. The dispensing system of claim 10, wherein one or more of the plurality of drone dispensers includes a sheet material dispenser, and/or one or more of the plurality of drone dispensers includes a liquid dispenser.

13. The dispensing system of claim 10, wherein the plurality of drone dispensers transmits one or more alerts or notifications to the lead dispenser if the one or more drone dispensers are experiencing an error condition, a low power condition, and/or a low supply condition, and wherein the lead dispenser transmits the one or more alerts or notifications from the plurality of drone dispensers to the network.

14. The dispensing system of claim 10, wherein the lead dispenser includes a long range transmitter/receiver that facilitates communication between the lead dispenser and the network.

15. The dispensing system of claim 10, wherein each of the drone dispensers further comprises a switching mechanism between the power source and the controller and in communication with the passive infrared sensor; wherein when the passive infrared radiation sensor thereof does not capture infrared radiation within the prescribed detection range, area, or zone, the switching mechanism is operated so as to disconnect the drone dispenser controller of the drone dispenser from the power source.

16. A dispenser, comprising:
a supply of liquid or sheet material;
a dispensing mechanism in communication with the supply and configured to dispense prescribed amounts of the supply of liquid or sheet material;
a proximity sensor configured to detect a presence of a user proximate the dispenser;
a dispenser controller in communication with the dispensing mechanism and the proximity sensor, the dispenser controller configured to activate the dispensing mechanism to dispense the prescribed amounts of the supply upon receipt of one or more signals from the proximity sensor indicative of the presence of the user proximate the dispenser;
a power source supplying power to the dispenser controller, dispensing mechanism and proximity sensor; and
a power management system in communication with the dispenser controller, the power management system comprising:
at least one passive infrared radiation sensor configured to detect infrared radiation emitted by one or more users within a prescribed detection range, area, or zone of the dispenser; and
a passive infrared radiation sensor controller integrated with the passive infrared radiation sensor and in communication with the dispenser controller;

wherein, when the passive infrared radiation sensor does not capture infrared radiation within the prescribed detection range, area, or zone, the passive infrared radiation sensor controller communicates with the dispenser controller to place the dispenser in a low power state in which the dispenser controller, the dispensing mechanism, and the proximity sensor are disconnected from the power source, with the passive infrared sensor and the passive infrared radiation sensor controller remaining connected to the power source and to the dispenser controller; and
wherein, when the at least one passive infrared radiation sensor captures infrared radiation within the prescribed detection range, area, or zone, the passive infrared radiation sensor controller sends one or more signals to the dispenser controller to initiate a start-up sequence, and connect the dispenser controller, the dispensing mechanism, and the proximity sensor to the power source.

17. The dispenser of claim 16, wherein:
when the passive infrared radiation sensor does not capture infrared radiation within the prescribed detection range, area, or zone, the passive infrared radiation sensor controller is configured to output one or more low level signals to the dispenser controller; and
wherein upon receipt of the one or more low level signals from the passive infrared radiation sensor controller by the dispenser controller, the dispenser controller initiates a shutdown sequence to complete any ongoing work, functions, or operations of the dispenser controller, and upon completion of the shutdown sequence, the dispenser controller, the dispensing mechanism, and the proximity sensor are disconnected from the power source.

18. The dispenser of claim 16, further comprising a switching mechanism between the dispenser controller and the power source and in communication with the passive infrared sensor; wherein, when the at least one passive infrared radiation sensor does not capture infrared radiation within the prescribed detection range, area, or zone, the switching mechanism is operated to disconnect the controller, the dispensing mechanism, and the proximity sensor from the power source; and wherein, when the at least one passive infrared radiation sensor captures infrared radiation within the prescribed detection range, area, or zone, the switching mechanism is operated to connect the dispenser controller, the dispensing mechanism, and the proximity sensor to the power source.

19. The dispenser of claim 16, further comprising a timer integrated with the passive infrared radiation sensor controller, wherein the timer is activated when the passive infrared radiation sensor does not detect infrared radiation within the prescribed detection range, area, or zone; and wherein upon expiration of the timer, the power source is disconnected from the dispenser controller, the dispensing mechanism, and the proximity sensor.

* * * * *